(12) United States Patent
Gabriel et al.

(10) Patent No.: US 6,531,612 B2
(45) Date of Patent: Mar. 11, 2003

(54) NITRILE DERIVATIVES THAT INHIBIT CATHEPSIN K

(75) Inventors: Tobias Gabriel, Loerrach (DE); Michael Pech, Hartheim (DE); Sabine Wallbaum, Ostfildern (DE)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/745,675

(22) Filed: Dec. 21, 2000

(65) Prior Publication Data

US 2001/0008901 A1 Jul. 19, 2001

(30) Foreign Application Priority Data

Dec. 24, 1999 (EP) .............................. 99125857

(51) Int. Cl.[7] .................. C07D 207/16; C07D 207/48; C07D 209/02
(52) U.S. Cl. ................. 548/452; 548/200; 548/201; 548/215; 548/468; 548/518; 548/526; 548/537; 548/538
(58) Field of Search .............................. 548/537, 538, 548/518, 526, 452, 468

(56) References Cited

U.S. PATENT DOCUMENTS 4,927,909 A  5/1990  Stueber

FOREIGN PATENT DOCUMENTS

| WO | WO 98 01133 | 1/1998 |
|----|-------------|--------|
| WO | WO 99 17792 | 4/1999 |
| WO | 99/24460    | 5/1999 |
| WO | WO 00 55125 | 9/2000 |
| WO | WO 00 55126 | 9/2000 |

OTHER PUBLICATIONS

Bromme, Drug News Perspect, 12, pp. 73–82 (1999).
Chapman et al., Annu. Rev. Phys., 59, pp. 63–88 (1997).
Tezuka et al., J. Biol. Chem. 269, pp. 1106–1109 (1994).
Lerner et al., J. Bone Min. Res., 7, pp. 433–440 (1992).
Everts et al., J. Cell. Physiol., 150, pp. 221–231 (1992).
Hummel et al., J. Rheumatol., 25, pp. 1887–1894 (1998).
Libby et al., J. Clin. Invest., 102, pp. 576–583 (1998).
Littlewood–Evans et al., Cancer Res., 57, pp. 5386–5390 (1997).
Schirmeister et al., Chem. Rev., 97, pp. 133–171 (1997).
Veber et al., Proc. Natl. Acad. Sci. USA, 94, pp. 14249–14254 (1997).
Wiederanders et al., Eur. J. Biochem., 250, pp. 745–750, (1997).

*Primary Examiner*—Laura L. Stockton
(74) *Attorney, Agent, or Firm*—George W. Johnston; Patricia S. Rocha-Tramaloni; Lyman H. Smith

(57) ABSTRACT

Compounds of the formula:

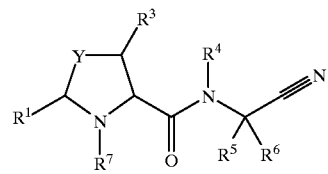

(I)

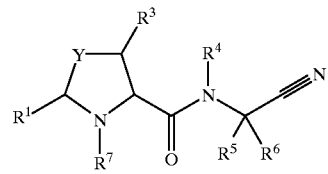

(I)

wherein $R^1$ to $R^7$ and Y are as defined in the specification, and pharmaceutically acceptable salts and/or pharmaceutically acceptable esters thereof, are useful for treating diseases associated with cystein proteases, such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease.

184 Claims, No Drawings

NITRILE DERIVATIVES THAT INHIBIT CATHEPSIN K

BACKGROUND OF THE INVENTION

1. Field

The present invention relates to novel nitrile derivatives, their manufacture and use as medicaments. In particular, the invention relates to novel nitrile derivatives of formula (I)

2. Description

Cysteine proteases have been viewed as lysosomal mediators of terminal protein degradation. Several newly discovered members of this enzyme class, however, are regulated proteases with limited tissue expression, which implies specific roles in cellular physiology and thus would allow a specific targeting of these activities without interfering with the general lysosomal protein degragation. Development of inhibitors of specific cysteine proteases promises to provide new drugs for modifying immunity, osteoporosis, neurodegeneration, chronic inflammation, cancer and malaria (Brömme, *Drug News Perspect* 1999, 12(2), 73–82; Chapman et al., *Annu. Rev. Phys.* 1997, 59, 63–88).

Cysteine proteases can be grouped into two superfamilies: the family of enzymes related to interleukin 1β converting enzyme (ICE), and the papain superfamily of cysteine proteases. Presently there are at least 12 human proteases of the papain family from which sequences have been obtained (cathepsin B, L, H, S, O, K, C, W, F, V(L2), Z(X) and bleomycin hydrolase). Cathepsin K was first discovered as a cDNA prominent in rabbit osteoclasts and referred to as OC-2 (Tezuka et al., *J. Biol. Chem.* 1994, 269, 1106–1109). Recent observations indicate that cathepsin K is a very potent mammalian elastase. Cathepsin K, as well as cathepsins S and L, are also potent collagenases and gelatinases. Macrophages appear capable of mobilizing the active proteases within endosomal and/or lysosomal compartments to the cell surface under special circumstances. In this case, the cell surface/substrate interface becomes a compartment from which endogenous inhibitors are excluded and can be viewed as a physiological extension of the lysosome. This type of physiology is an innate trait of osteoclasts, a bone macrophage, and may also be exploited by other macrophages or cells in the context of inflammation. The abundance of cathepsin K in osteoclasts suggests that cathepsin K plays an important role in bone resorption. Studies revealed that cathepsin K is the predominant cysteine protease in osteoclasts and is specifically expressed in human osteoclasts. A correlation between inhibition of cysteine protease activity and bone resorption has been reported (Lerner et al., *J. Bone Min. Res.* 1992, 7, 433; Everts et al., *J. Cell. Physiol.* 1992, 150, 221). Cathepsin K has been detected in synovial fibroblasts of RA patients, as well as in mouse hypertrophic chondrocytes (Hummel et al., *J. Rheumatol.* 1998, 25(10), 1887–1894.). Both results indicate a direct role of cathepsin K in cartilage erosion. P. Libby (Libby et al., *J. Clin. Invest.* 1998, 102 (3), 576–583) reported that normal arteries contain little or no cathepsin K or S whereas macrophages in atheroma contained abundant immunoreactive cathepsins K and S. Most of the elastolytic activity of tissue extracts associated with human atheroma compared to non-atherosclerotic arteries could be inhibited with E64, a non-selective cysteine protease inhibitor.

Tumor progression and metastasis are characterized by the invasion of tumors into adjacent tissues as well as by the dissociation of cancer cells from primary tumors and the infiltration of metastatic cells into organs. These processes are associated with the degragation of extracellular matrix proteins and thus require proteolytic activity. Cathepsin K has been identified in primary breast tumors, as well as in breast tumor-derived bone metastasis (Littlewood-Evans et al., *Cancer Res.* 1997, 57, 5386–5390).

Different classes of compounds, such as aldehydes, α-ketocarbonyl compounds, halomethyl ketones, diazomethyl ketones, (acyloxy)methyl ketones, ketomethylsulfonium salts, epoxy succinyl compounds, vinyl sulfones, aminoketones, and hydrazides have been identified as cysteine protease inhibitors (Schirmeister et al., *Chem. Rev.* 1997, 97, 133–171; Veber et al., *Proc. Natl. Acad. Sci. USA* 1997, 94, 14249–14254). The shortcomings these compounds suffer from include lack of selectivity, poor solubility, rapid plasma clearance and cytotoxicity. A need therefore exists for novel inhibitors useful in treating diseases caused by pathological levels of proteases, such as cysteine proteases, including cathepsins, and especially cathepsin K. Therefore, a need exists for compounds that are selective inhibitors of cathepsin K.

SUMMARY OF THE INVENTION

The subject invention provides compounds of the formula:

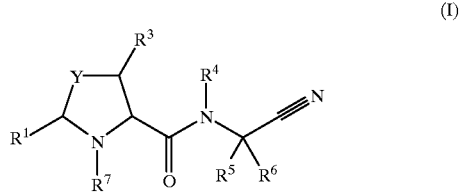

(I)

wherein

Y is O, S, or CH—$R^2$;

$R^1$ and $R^3$ are each independently hydrogen or methyl and $R^2$ is hydrogen, or $R^1$ is hydrogen and $R^2$ and $R^3$ together are —$CH_2$— thus forming a cyclopropyl ring;

$R^4$, $R^5$ are each independently hydrogen or lower-alkyl;

$R^6$ is cycloalkyl, aryl, aryl-lower-alkyl, heteroaryl, or heteroaryl-lower-alkyl;

$R^7$ is —CO—$R^a$, —$SO_2$—$R^b$ or —CS—NH—$R^c$, wherein $R^a$ is lower-alkyl, cycloalkyl, cycloalkyl-lower-alkyl, cycloalkyl-lower-alkoxy, aryl, heteroaryl, aryl-lower-alkyl, aryl-lower-alkoxy, heteroaryl-lower-alkoxy, aryl-lower-alkoxy-lower-alkyl, aryloxy-lower-alkyl, arylthio-lower-alkyl, aryl-lower-alkenyl, aryl-cycloalkyl, or $R^d$—NH, $R^b$ is lower-alkyl, cycloalkyl, cycloalkyl-lower-alkyl, aryl, heteroaryl, aryl-lower-alkyl, or aryl-lower-alkenyl, $R^c$ is lower-alkyl, cycloalkyl, cycloalkyl-lower-alkyl, aryl, heteroaryl, aryl-lower-alkyl, or heteroaryl-lower-alkyl, $R^d$ is aryl-lower-alkyl;

or a pharmaceutically acceptable salt or ester thereof.

A preferred group of compounds are of the formula:

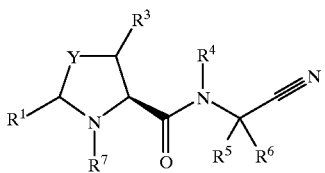

(Ia)

wherein Y, $R^1$, $R^3$, $R^4$, $R^5$, $R^6$ and $R^7$ are as defined above.

Another favored group of compounds are of the formula:

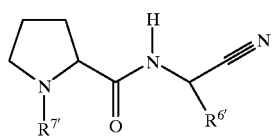

(I')

wherein
$R^{6'}$ is aryl;
$R^{7'}$ is —CO—$R^{a'}$ or —CS—NH—$R^{c'}$, wherein
$R^{a'}$ is cycloalkyl-lower-alkyl, aryl-lower-alkyl, aryl-lower-alkoxy, aryl-lower-alkoxy-lower-alkyl, aryloxy-lower-alkyl, and
$R^{c'}$ is heteroaryl-lower-alkyl;
or a pharmaceutically acceptable salt or ester thereof.

DETAILED DESCRIPTION OF THE PREFERRED EMBODIMENTS

The subject invention will now be described in terms of its preferred embodiments. These embodiments are set forth to aid in understanding the invention but are not to be construed as limiting.

The present invention also relates to processes for the preparation of the compounds of formula (I).

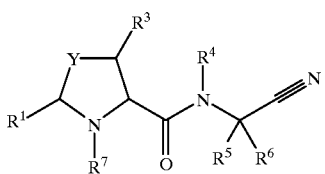

(I)

wherein
Y represents O, S, or CH—$R^2$,
$R^1$ and $R^3$ independently from each other represent hydrogen or methyl and $R^2$ represents hydrogen, or $R^1$ represents hydrogen and $R^2$ and $R^3$ together are —$CH_2$— to form a cyclopropyl ring,
$R^4$, $R^5$ independently from each other represent hydrogen or lower-alkyl,
$R^6$ represents cycloalkyl, aryl, aryl-lower-alkyl, heteroaryl, or heteroaryl-lower-alkyl,
$R^7$ represents —CO—$R^a$, —$SO_2$—$R^b$ or —CS—NH—$R^c$, wherein
$R^a$ represents lower-alkyl, cycloalkyl, cycloalkyl-lower-alkyl, cycloalkyl-lower-alkoxy, aryl, heteroaryl, aryl-lower-alkyl, aryl-lower-alkoxy, heteroaryl-lower-alkoxy, aryl-lower-alkoxy-lower-alkyl, aryloxy-lower-alkyl, arylthio-lower-alkyl, aryl-lower-alkenyl, aryl-cycloalkyl, or $R^d$—NH,
$R^b$ represents lower-alkyl, cycloalkyl, cycloalkyl-lower-alkyl, aryl, heteroaryl, aryl-lower-alkyl, or aryl-lower-alkenyl,
$R^c$ represents lower-alkyl, cycloalkyl, cycloalkyl-lower-alkyl, aryl, heteroaryl, aryl-lower-alkyl, or heteroaryl-lower-alkyl,
$R^d$ represents aryl-lower-alkyl,
and pharmaceutically acceptable salts and/or pharmaceutically acceptable esters thereof.

The nitriles derivatives of the present invention have an inhibitory activity on cysteine proteases, more paticulary on cysteine proteases of the papain superfamily, even more paticularly on cysteine proteases of the cathepsin family, most particularly on cathepsin K. It was surprisingly found, that this inhibiting effect on cathepsin K is selective with respect to other cathepsins. While compounds of formula (I) very efficiently inhibit cathepsin K, the inhibition of other protease inhibitors such as cathepsin S, cathepsin L and cathepsin B is much weaker. Therefore the new compounds of formula (I) are usefull for specifically inhibiting cathepsin K. They can accordingly be used for the treatment of disorders which are associated with cysteine proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease. Accordingly, the present invention relates to a method for the prophylactic and/or therapeutic treatment of diseases which are associated with cystein proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease, which method comprises administering a compound of formula (I) to a human being or an animal. The present invention also relates to pharmaceutical compositions comprising a compound of formula (I) and a pharmaceutically acceptable carrier and/or adjuvant. Furthermore, the present invention relates to the use of such compounds for the preparation of medicaments for the treatment of disorders which are associated with cystein proteases.

Unless otherwise indicated the following definitions are set forth to illustrate and define the meaning and scope of the various terms used to describe the invention herein.

In this specification the term "lower" is used to mean a group consisting of one to seven, preferably of one to four carbon atom(s).

The term "alkyl" refers to a branched or straight chain monovalent saturated aliphatic hydrocarbon radical of one to twenty carbon atoms, preferably one to sixteen carbon atoms.

The term "lower-alkyl" refers to a branched or straight chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like.

The term "cycloalkyl" refers to a monovalent carbocyclic radical of 3 to 10 carbon atoms, preferably 3 to 6 carbon atoms.

The term "halogen" refers to fluorine, chlorine, bromine and iodine, with fluorine, chlorine and bromine being preferred and chlorine and bromine being more preferred.

The term "alkoxy" refers to the group R'—O—, wherein R' is an alkyl. The term "lower-alkoxy" refers to the group R'—O—, wherein R' is a lower-alkyl.

The term "aryl" relates to the phenyl or naphthyl group which can optionally be mono- or multiply-substituted by alkyl, halogen, hydroxy, alkoxy, —O—$(CH_2)_{1-7}$—O—, aryloxy, or arylalkoxy. Substitution in meta- or in meta- and para-position is preferred. Preferred substituents are lower-alkyl, fluorine, chlorine, bromine, lower-alkoxy, methylenedioxy, and aryl-lower-alkoxy. More preferred substituents are chlorine, bromine, methoxy, and benzyloxy. Another preferred substituted phenyl group is the benzo[1,3]dioxol-5-yl group.

The term "heteroaryl" refers to an aromatic 5- or 6-membered ring which can contain 1 or 2 atoms selected from nitrogen, oxygen or sulphur such as furyl, pyridyl, 1,2-, 1,3- and 1,4-diazinyl, thienyl, isoxazolyl, oxazolyl, imidazolyl, pyrrolyl, with furyl and thienyl being preferred. The term "heteroaryl" further refers to bicyclic heteroaromatic ring systems such as e.g. indolyl. A heteroaryl group may have a substitution pattern as described earlier in connection with the term "aryl".

An aryl-lower-alkyl group may optionally comprise a second aryl group, e.g. a phenyl group, at the lower-alkyl moiety.

The term "aryloxy" relates to a group aryl-O—. The term "arylthio" relates to a group aryl-S—.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

The term "pharmaceutically acceptable esters" embraces esters of the compounds of formula (1), in which hydroxy groups have been converted to the corresponding esters with inorganic or organic acids such as nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

In detail, the present invention refers to compounds of formula (I)

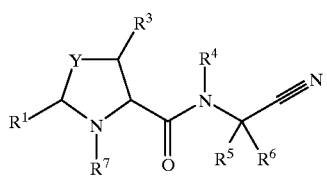

(I)

wherein

Y represents O, S, or CH—$R^2$, $R^1$ and $R^3$ independently from each other represent hydrogen or methyl and $R^2$ represents hydrogen, or $R^1$ represents hydrogen and $R^2$ and $R^3$ together are —$CH_2$— to form a cyclopropyl ring, $R^4$, $R^5$ independently from each other represent hydrogen or lower-alkyl, $R^6$ represents cycloalkyl, aryl, aryl-lower-alkyl, heteroaryl, or heteroaryl-lower-alkyl, $R^7$ represents —CO—$R^a$, —$SO_2$—$R^b$ or —CS—NH—$R^c$, wherein $R^a$ represents lower-alkyl, cycloalkyl, cycloalkyl-lower-alkyl, cycloalkyl-lower-alkoxy, aryl, heteroaryl, aryl-lower-alkyl, aryl-lower-alkoxy, heteroaryl-lower-alkoxy, aryl-lower-alkoxy-lower-alkyl, aryloxy-lower-alkyl, arylthio-lower-alkyl, aryl-lower-alkenyl, aryl-cycloalkyl, or $R^d$—NH, $R^b$ represents lower-alkyl, cycloalkyl, cycloalkyl-lower-alkyl, aryl, heteroaryl, aryl-lower-alkyl, or aryl-lower-alkenyl, $R^c$ represents lower-alkyl, cycloalkyl, cycloalkyl-lower-alkyl, aryl, heteroaryl, aryl-lower-alkyl, or heteroaryl-lower-alkyl, $R^d$ represents aryl-lower-alkyl, and pharmaceutically acceptable salts and/or pharmaceutically acceptable esters thereof.

In a preferred embodiment, the present invention relates to compounds as described above, wherein $R^7$ represents —CO—$R^a$, —$SO_2$—$R^b$ or —CS—NH—$R^c$, wherein $R^a$ represents lower-alkyl, cycloalkyl, cycloalkyl-lower-alkyl, cycloalkyl-lower-alkoxy, aryl, heteroaryl, aryl-lower-alkyl, aryl-lower-alkoxy, heteroaryl-lower-alkoxy, aryl-lower-alkoxy-lower-alkyl, or $R^d$—NH, $R^b$ represents lower-alkyl, cycloalkyl, cycloalkyl-lower-alkyl, aryl, heteroaryl, aryl-lower-alkyl, or aryl-lower-alkenyl, $R^c$ represents lower-alkyl, cycloalkyl, cycloalkyl-lower-alkyl, aryl, heteroaryl, aryl-lower-alkyl, or heteroaryl-lower-alkyl, $R^d$ represents aryl-lower-alkyl, and pharmaceutically acceptable salts and/or pharmaceutically acceptable esters thereof.

The compounds of formula (I) have at least 2 asymmetric carbon atoms and can exist in the form of optically pure enantiomers or as racemates. The invention embraces all of these forms. Preferred compounds of formula (I) are compounds of formula (Ia) which are derived from the corresponding S-proline derivatives.

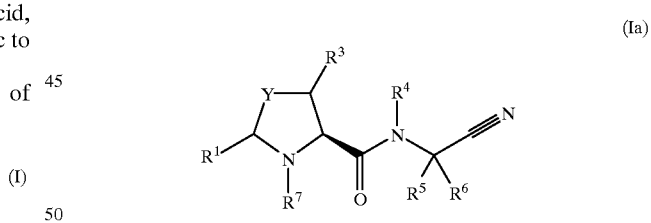

(Ia)

wherein Y, $R^1$, $R^3$, $R^4$, $R^5$, $R^6$ and $R^7$ are as defined above, and pharmaceutically acceptable salts and/or pharmaceutically acceptable esters thereof.

Compounds of formula (I) in which Y represents CH—$R^2$ are preferred, with those wherein $R^2$ is hydrogen being particularly preferred. Compounds of formula (I) in which $R^1$, $R^3$, $R^4$ and/or $R^5$ represent hydrogen are also preferred. Another preferred embodiement refers to compounds of formula (I) in which $R^6$ is phenyl, furanyl, thiophenyl, or pyrrolyl, optionally substituted with alkyl, halogen, hydroxy, alkoxy, —O—$(CH_2)_{1-7}$—O—, aryloxy, or arylalkoxy. Further, compounds of formula (I) in which $R^6$ represents phenyl, phenyl substituted in meta-position, phenyl substituted in meta- and in para-position or benzo[1,3]dioxol-5-yl are also preferred with 3-methoxy-phenyl, 3,4-dimethoxy-phenyl, 4-benzyloxy-3-methoxy-phenyl, 3-chloro-phenyl, 3-bromo-phenyl, or benzo[1,3]dioxol-5-yl being especially preferred.

Compounds of formula (I) in which R⁷ represents —CO—Rᵃ and Rᵃ is as defined above are preferred. Compounds of formula (I) in which R⁷ represents —CO—Rᵃ and Rᵃ is benzyloxy, cyclopentyl-ethylene, or benzyloxymethylene are especially preferred. Further, compounds of formula (I) in which R⁷ represents —CO—Rᵃ and Rᵃ is 3-bromobenzyl, 4-bromobenzyl, 4-chlorobenzyl, 4-fluorobenzyl, or 2-methyl-phenyloxymethylene are also especially preferred. A further preferred embodiement are compounds of formula (I) in which R⁷ represents —CS—NH—Rᶜ and Rᶜ is as defined above. Compounds of formula (I) in which R⁷ represents —CS—NH—Rᶜ and Rᶜ is benzyl, 3-fluorobenzyl, or furan-2-yl-methylene are especially preferred. Another preferred embodiement relates to compounds of formula (I), wherein R⁷ represents —SO₂—Rᵇ and Rᵇ is as defined above, with those in which Rᵇ is naphthyl being particularly preferred.

Preferred compounds of formula 1 are (1RS,2RS,5SR)-2-{[(RS)- or -[(SR)-Cyano-(3,4-dimethoxy-phenyl)-methyl]-carbamoyl}-3-aza-bicyclo[3.1.0]hexane-3-carboxylic acid benzyl ester, (S)-2-[(R)-(Cyano-phenyl-methyl)-carbamoyl]-pyrrolidine-1-carboxylic acid benzyl ester, (S)-2-[(S)-(Cyano-phenyl-methyl)-carbamoyl]-pyrrolidine-1-carboxylic acid benzyl ester, (S)-1-(3-methyl-butyryl)-pyrrolidine-2-carboxylic acid (R)- and (S)-(cyano-phenyl-methyl)-amide, (S)-2-{(S)- and (R)-[Cyano-(3-methoxy-phenyl)-methyl]-carbamoyl}-pyrrolidine-1-carboxylic acid benzyl ester, (S)-2-{(S)- and (R)-[Cyano-(3-hydroxy-phenyl)-methyl]-carbamoyl}-pyrrolidine-1-carboxylic acid benzyl ester, (S)-2-[(R)- and (S)-(Cyano-cyclopropyl-methyl)-carbamoyl]-pyrrolidine-1-carboxylic acid benzyl ester, (S)-2-[(R)- and (S)-(Benzo[1,3]dioxol-5-yl-cyano-methyl)-carbamoyl]-pyrrolidine-1-carboxylic acidbenzyl ester, (R)-4-{(R)- and (S)-[Cyano-(3,4-dimethoxy-phenyl)-methyl]-carbamoyl}-thiazolidine-3-carboxylic acid benzyl ester, (2S,3R)-2-{(R)- and (S)-[Cyano-(3,4-dimethoxy-phenyl)-methyl]-carbamoyl}-3-methyl-pyrrolidine-1-carboxylic acid benzyl ester, (S)-1-Benzylthiocarbamoyl-pyrrolidine-2-carboxylic acid ((R)- and (S)-benzo[1,3]dioxol-5-yl-cyano-methyl)-amide, (S)-1-Benzylthiocarbamoyl-pyrrolidine-2-carboxylic acid [(R)- and (S)-cyano-(3,4-dimethoxy-phenyl)-methyl]-amide, (S)-1-[(Furan-2-ylmethyl)-thiocarbamoyl]-pyrrolidine-2-carboxylic acid [(R)- and (S)-cyano-(3,4-dimethoxy-phenyl)-methyl]-amide, (S)-1-Benzylthiocarbamoyl-pyrrolidine-2-carboxylic acid [(R)- and (S)-(3-chloro-phenyl)-cyano-methyl]-amide, (S)-1-(3-Fluoro-benzylthiocarbamoyl)-pyrrolidine-2-carboxylic acid [(R)- and (S)-(3-chloro-phenyl)-cyano-methyl]-amide, (S)-2-((R)- and (S)-1-Cyano-3-phenyl-propylcarbamoyl)-pyrrolidine-1-carboxylic acid benzyl ester, (R)-4-{(R)- and (S)-[(4-Chloro-phenyl)-cyano-methyl]-carbamoyl}-thiazolidine-3-carboxylic acid benzyl ester, (S)-2-{(R)- and (S)-[(3-Chloro-phenyl)-cyano-methyl]-carbamoyl}-pyrrolidine-1-carboxylic acid benzyl ester, (S)-2-[(R)- and (S)-(Cyano-o-tolyl-methyl)-carbamoyl]-pyrrolidine-1-carboxylic acid benzyl ester, (S)-2-{(R)- and (S)-[Cyano-(2,4-dimethoxy-phenyl)-methyl]-carbamoyl}-pyrrolidine-1-carboxylic acid benzyl ester, (S)-2-{(R)- and (S)-[(3-Bromo-phenyl)-cyano-methyl]-carbamoyl}-pyrrolidine-1-carboxylic acid benzyl ester, (S)-2-{(R)- and (S)-[Cyano-(3-fluoro-phenyl)-methyl]-carbamoyl}-pyrrolidine-1-carboxylic acid benzyl ester, (S)-2-[(R)- and (S)-(Cyano-m-tolyl-methyl)-carbamoyl]-pyrrolidine-1-carboxylic acid benzyl ester, (S)-2-{(R)- and (S)-[(4-Bromo-phenyl)-cyano-methyl]-carbamoyl}-pyrrolidine-1-carboxylic acid benzyl ester, (S)-2-{(R)- and (S)-[Cyano-(3,4,5-trimethoxy-phenyl)-methyl]-carbamoyl}-pyrrolidine-1-carboxylic acid benzyl ester, (S)-2-{(R)- and (S)-[Cyano-(3-phenoxy-phenyl)-methyl]-carbamoyl}-pyrrolidine-1-carboxylic acid benzyl ester, (S)-2-{(R)- and (S)-[(4-Benzyloxy-3-methoxy-phenyl)-cyano-methyl]-carbamoyl}-pyrrolidine-1-carboxylic acid benzyl ester, (S)-1-(Naphthalene-2-sulfonyl)-pyrrolidine-2-carboxylic acid [(R)- and (S)-cyano-(3,4-dimethoxy-phenyl)-methyl]-amide, (S)-1-(Naphthalene-1-sulfonyl)-pyrrolidine-2-carboxylic acid ((R)- and (S)-benzo[1,3]dioxol-5-yl-cyano-methyl)-amide, (S)-1-(3-Cyclopentyl-propionyl)-pyrrolidine-2-carboxylic acid ((R)- and (S)-benzo[1,3]dioxol-5-yl-cyano-methyl)-amide, (S)-1-Benzyloxyacetyl-pyrrolidine-2-carboxylic acid ((R)- and (S)-benzo[1,3]dioxol-5-yl-cyano-methyl)-amide, (S)-1-(5-Dimethylamino-naphthalene-1-sulfonyl)-pyrrolidine-2-carboxylic acid [(R)- and (S)-cyano-(3,4-dimethoxy-phenyl)-methyl]-amide, (S)-1-(Naphthalene-1-sulfonyl)-pyrrolidine-2-carboxylic acid [(R)- and (S)-cyano-(3,4-dimethoxy-phenyl)-methyl]-amide, (S)-1-(Naphthalene-2-carbonyl)-pyrrolidine-2-carboxylic acid [(R)- and (S)-cyano-(3,4-dimethoxy-phenyl)-methyl]-amide, (S)-1-(Naphthalene-1-carbonyl)-pyrrolidine-2-carboxylic acid [(R)- and (S)-cyano-(3,4-dimethoxy-phenyl)-methyl]-amide, (S)-1-(3-Cyclopentyl-propionyl)-pyrrolidine-2-carboxylic acid [(R)- and (S)-cyano-(3,4-dimethoxy-phenyl)-methyl]-amide, (S)-1-Benzyloxyacetyl-pyrrolidine-2-carboxylic acid [(R)- and (S)-cyano-(3,4-dimethoxy-phenyl)-methyl]-amide, (S)-1-(Naphthalene-1-carbonyl)-pyrrolidine-2-carboxylic acid [(R)- and (S)-(3-chloro-phenyl)-cyano-methyl]-amide, (S)-1-(3-Cyclopentyl-propionyl)-pyrrolidine-2-carboxylic acid [(R)- and (S)-(3-chloro-phenyl)-cyano-methyl]-amide, (S)-1-Phenylacetyl-pyrrolidine-2-carboxylic acid [(R)- and (S)-(3-chloro-phenyl)-cyano-methyl]-amide, (S)-1-Benzyloxyacetyl-pyrrolidine-2-carboxylic acid [(R)- and (S)-(3-chloro-phenyl)-cyano-methyl]-amide, (S)-Pyrrolidine-1,2-dicarboxylic acid 2-{[(R)- and (S)-(3-chloro-phenyl)-cyano-methyl]-amide}1-[(R)-(1-naphthalen-1-yl-ethyl)-amide], (S)-1-(Naphthalene-1-carbonyl)-pyrrolidine-2-carboxylic acid [(R)- and (S)-(3-bromo-phenyl)-cyano-methyl]-amide, (S)-1-Phenylacetyl-pyrrolidine-2-carboxylic acid [(R)- and (S)-(3-bromo-phenyl)-cyano-methyl]-amide, (S)-1-Benzyloxyacetyl-pyrrolidine-2-carboxylic acid [(R)- and (S)-(3-bromo-phenyl)-cyano-methyl]-amide, (S)-Pyrrolidine-1,2-dicarboxylic acid 2-{[(R)- and (S)-(3-bromo-phenyl)-cyano-methyl]-amide}1-[(R)-(1-naphthalen-1-yl-ethyl)-amide], (S)-1-(3-Cyclopentyl-propionyl)-pyrrolidine-2-carboxylic acid [(R)- and (S)-cyano-(3-methoxy-phenyl)-methyl]-amide, (S)-1-Phenylacetyl-pyrrolidine-2-carboxylic acid [(R)- and (S)-cyano-(3-methoxy-phenyl)-methyl]-amide, (S)-1-Benzyloxyacetyl-pyrrolidine-2-carboxylic acid [(R)- and (S)-cyano-(3-methoxy-phenyl)-methyl]-amide, 2-((R)- and (S)-1-Cyano-3-phenyl-propylcarbamoyl)-pyrrolidine-1-carboxylic acid benzyl ester, (S)-2-{(R)- and (S)-[Cyano-(3,4-dimethoxy-phenyl)-methyl]-carbamoyl}-pyrrolidine-1-carboxylic acid benzyl ester, (S)-1-(2-Phenyl-ethenesulfonyl)-pyrrolidine-2-carboxylic acid ((R)- and (S)-benzo[1,3]dioxol-5-yl-cyano-methyl)-amide, (S)-Pyrrolidine-1,2-dicarboxylic acid 2-{(R)- and (S)-[cyano-(3,4-dimethoxy-phenyl)-methyl]-amide}1-[(S)-(1-naphthalen-1-yl-ethyl)-amide], (S)-1-(2-Phenyl-ethenesulfonyl)-pyrrolidine-2-carboxylic acid [(R)- and (S)-cyano-(3,4-dimethoxy-phenyl)-methyl]-amide, and pharmaceutically acceptable esters thereof.

Other preferred compounds of formula 1 are (S)-1-[2-(3-Bromo-phenyl)-ethanoyl]-pyrrolidine-2-carboxylic acid (1-benzo[1,3]dioxol-5-yl-1-cyano-methyl)-amide, (S)-1-[2-(3-Bromo-phenyl)-ethanoyl]-pyrrolidine-2-carboxylic acid [1-cyano-1-(3,4-dimethoxy-phenyl)-methyl]-amide, (S)-1-[2-(4-Bromo-phenyl)-ethanoyl]-pyrrolidine-2-carboxylic acid [1-cyano-1-(3,4-dimethoxy-phenyl)-methyl]-amide, (S)-1-[2-(4-Chloro-phenyl)-ethanoyl]-pyrrolidine-2-carboxylic acid [1-(3-chloro-phenyl)-1-cyano-methyl]-amide, (S)-1-[2-(4-Fluoro-phenyl)-ethanoyl]-pyrrolidine-2-carboxylic acid (1-benzo[1,3]dioxol-5-yl-1-cyano-methyl)-amide, (S)-1-[2-(4-Chloro-phenyl)-ethanoyl]-pyrrolidine-2-carboxylic acid [1-cyano-1-(3,4-dimethoxy-phenyl)-methyl]-amide, (S)-1-(2-o-Tolyloxy-ethanoyl)-pyrrolidine-2-carboxylic acid [1-cyano-1-(3,4-dimethoxy-phenyl)-methyl]-amide, (S)-1-(2-o-Tolyloxy-ethanoyl)-pyrrolidine-2-carboxylic acid (1-benzo[1,3]dioxol-5-yl-1-cyano-methyl)-amide, (S)-1-[2-(4-Fluoro-phenyl)-ethanoyl]-pyrrolidine-2-carboxylic acid [1-cyano-1-(3,4-dimethoxy-phenyl)-methyl]-amide, (S)-1-[2-(4-Bromo-phenyl)-ethanoyl]-pyrrolidine-2-carboxylic acid (1-benzo[1,3]dioxol-5-yl-1-cyano-methyl)-amide, (S)-1-[2-(4-Bromo-phenyl)-ethanoyl]-pyrrolidine-2-carboxylic acid [1-(3-chloro-phenyl)-1-cyano-methyl]-amide, (S)-1-[2-(4-Iodo-phenyl)-ethanoyl]-pyrrolidine-2-carboxylic acid (1-benzo[1,3]dioxol-5-yl-1-cyano-methyl)-amide, (S)-1-[2-(4-Fluoro-phenyl)-ethanoyl]-pyrrolidine-2-carboxylic acid [1-(3-chloro-phenyl)-1-cyano-methyl]-amide, (S)-1-(4-Phenyl-butanoyl)-pyrrolidine-2-carboxylic acid [1-cyano-1-(3,4-dimethoxy-phenyl)-methyl]-amide, (S)-1-[2-(3-Bromo-phenyl)-ethanoyl]-pyrrolidine-2-carboxylic acid [1-(3-chloro-phenyl)-1-cyano-methyl]-amide, (S)-1-(2-Benzo[1,3]dioxol-5-yl-ethanoyl)-pyrrolidine-2-carboxylic acid [1-(3-chloro-phenyl)-1-cyano-methyl]-amide, (S)-1-(2-Phenoxy-ethanoyl)-pyrrolidine-2-carboxylic acid [1-cyano-1-(3,4-dimethoxy-phenyl)-methyl]-amide, (S)-1-(2-o-Tolyloxy-ethanoyl)-pyrrolidine-2-carboxylic acid [1-(3-chloro-phenyl)-1-cyano-methyl]-amide, (S)-1-(2-Benzo[1,3]dioxol-5-yl-ethanoyl)-pyrrolidine-2-carboxylic acid (1-benzo[1,3]dioxol-5-yl-1-cyano-methyl)-amide, (S)-1-(2-Phenoxy-ethanoyl)-pyrrolidine-2-carboxylic acid [1-(3-chloro-phenyl)-1-cyano-methyl]-amide, (S)-1-(2-Phenyl-ethanoyl)-pyrrolidine-2-carboxylic acid [1-(3-chloro-phenyl)-1-cyano-methyl]-amide, (S)-1-[2-(4-Fluoro-phenoxy)-ethanoyl]-pyrrolidine-2-carboxylic acid [1-cyano-1-(3,4-dimethoxy-phenyl)-methyl]-amide, (S)-1-(2-Benzo[1,3]dioxol-5-yl-ethanoyl)-pyrrolidine-2-carboxylic acid [1-cyano-1-(3,4-dimethoxy-phenyl)-methyl]-amide, (S)-1-(3-Phenyl-propanoyl)-pyrrolidine-2-carboxylic acid [1-cyano-1-(3,4-dimethoxy-phenyl)-methyl]-amide, (S)-1-[4-(3,4-Dimethoxy-phenyl)-butanoyl]-pyrrolidine-2-carboxylic acid (1-benzo[1,3]dioxol-5-yl-1-cyano-methyl)-amide, (S)-1-[4-(3,4-Dimethoxy-phenyl)-butanoyl]-pyrrolidine-2-carboxylic acid [1-(3-chloro-phenyl)-1-cyano-methyl]-amide, (S)-1-[2-(4-Iodo-phenyl)-ethanoyl]-pyrrolidine-2-carboxylic acid [1-cyano-1-(3,4-dimethoxy-phenyl)-methyl]-amide, (S)-1-[4-(3,4-Dimethoxy-phenyl)-butanoyl]-pyrrolidine-2-carboxylic acid [1-cyano-1-(3,4-dimethoxy-phenyl)-methyl]-amide, (S)-1-(3-1H-Indol-3-yl-propanoyl)-pyrrolidine-2-carboxylic acid [1-cyano-1-(3,4-dimethoxy-phenyl)-methyl]-amide, (S)-1-(4-Phenyl-butanoyl)-pyrrolidine-2-carboxylic acid (1-benzo[1,3]dioxol-5-yl-1-cyano-methyl)-amide, (S)-1-(2-Phenylsulfanyl-ethanoyl)-pyrrolidine-2-carboxylic acid [1-(3-chloro-phenyl)-1-cyano-methyl]-amide, (S)-1-(4-Cyclohexyl-butanoyl)-pyrrolidine-2-carboxylic acid [1-cyano-1-(3,4-dimethoxy-phenyl)-methyl]-amide, (S)-1-(3-Cyclohexyl-propanoyl)-pyrrolidine-2-carboxylic acid (1-benzo[1,3]dioxol-5-yl-1-cyano-methyl)-amide, (S)-1-[4-(4-Nitro-phenyl)-butanoyl]-pyrrolidine-2-carboxylic acid [1-cyano-1-(3,4-dimethoxy-phenyl)-methyl]-amide, (S)-1-[2-(4-Iodo-phenyl)-ethanoyl]-pyrrolidine-2-carboxylic acid [1-(3-chloro-phenyl)-1-cyano-methyl]-amide, (S)-1-[2-(2,4-Dimethyl-phenoxy)-ethanoyl]-pyrrolidine-2-carboxylic acid [1-(3-chloro-phenyl)-1-cyano-methyl]-amide, (S)-1-[4-(4-Nitro-phenyl)-butanoyl]-pyrrolidine-2-carboxylic acid [1-(3-chloro-phenyl)-1-cyano-methyl]-amide, (S)-1-(1-Naphthalen-1-yl-methanoyl)-pyrrolidine-2-carboxylic acid [1-(3-chloro-phenyl)-1-cyano-methyl]-amide, (S)-1-[2-(4-Methoxy-phenoxy)-ethanoyl]-pyrrolidine-2-carboxylic acid [1-(3-chloro-phenyl)-1-cyano-methyl]-amide, (S)-1-(2-Phenyl-ethanoyl)-pyrrolidine-2-carboxylic acid [1-cyano-1-(3,4-dimethoxy-phenyl)-methyl]-amide, (S)-1-[2-(2-Methoxy-phenoxy)-ethanoyl]-pyrrolidine-2-carboxylic acid [1-cyano-1-(3,4-dimethoxy-phenyl)-methyl]-amide, (S)-1-[2-(4-Methoxy-phenoxy)-ethanoyl]-pyrrolidine-2-carboxylic acid [1-cyano-1-(3,4-dimethoxy-phenyl)-methyl]-amide, (S)-1-(4-Cyclohexyl-butanoyl)-pyrrolidine-2-carboxylic acid (1-benzo[1,3]dioxol-5-yl-1-cyano-methyl)-amide, (S)-1-{1-[1-(4-Chloro-phenyl)-cyclopentyl]-methanoyl}-pyrrolidine-2-carboxylic acid [1-cyano-1-(3,4-dimethoxy-phenyl)-methyl]-amide, (S)-1-((Z)-3-Phenyl-allanoyl)-pyrrolidine-2-carboxylic acid [1-cyano-1-(3,4-dimethoxy-phenyl)-methyl]-amide, (S)-1-(2-Phenylsulfanyl-ethanoyl)-pyrrolidine-2-carboxylic acid [1-cyano-1-(3,4-dimethoxy-phenyl)-methyl]-amide, (S)-1-[2-(4-Fluoro-phenoxy)-ethanoyl]-pyrrolidine-2-carboxylic acid [1-(3-chloro-phenyl)-1-cyano-methyl]-amide, (S)-1-[2-(3-Methoxy-phenoxy)-ethanoyl]-pyrrolidine-2-carboxylic acid [1-cyano-1-(3,4-dimethoxy-phenyl)-methyl]-amide, (S)-1-(4-Phenyl-butanoyl)-pyrrolidine-2-carboxylic acid [1-(3-chloro-phenyl)-1-cyano-methyl]-amide, (S)-1-[2-(3,4,5-Trimethoxy-phenyl)-ethanoyl]-pyrrolidine-2-carboxylic acid [1-(3-chloro-phenyl)-1-cyano-methyl]-amide, (S)-1-(5-Phenyl-pentanoyl)-pyrrolidine-2-carboxylic acid [1-cyano-1-(3,4-dimethoxy-phenyl)-methyl]-amide, (S)-1-(1-Cyclopropyl-methanoyl)-pyrrolidine-2-carboxylic acid [1-cyano-1-(3,4-dimethoxy-phenyl)-methyl]-amide, (S)-1-[2-(4-Fluoro-phenoxy)-ethanoyl]-pyrrolidine-2-carboxylic acid (1-benzo[1,3]dioxol-5-yl-1-cyano-methyl)-amide, (S)-1-[2-(4-Chloro-phenoxy)-ethanoyl]-pyrrolidine-2-carboxylic acid [1-(3-chloro-phenyl)-1-cyano-methyl]-amide, (S)-1-(2-Phenyl-ethanoyl)-pyrrolidine-2-carboxylic acid [1-(3-chloro-phenyl)-1-cyano-methyl]-amide, (S)-1-(3,3-Diphenyl-propanoyl)-pyrrolidine-2-carboxylic acid [1-cyano-1-(3,4-dimethoxy-phenyl)-methyl]-amide, (S)-1-[2-(3-Methoxy-phenoxy)-ethanoyl]-pyrrolidine-2-carboxylic acid (1-benzo[1,3]dioxol-5-yl-1-cyano-methyl)-amide, (S)-1-[2-(4-Ethoxy-phenyl)-ethanoyl]-pyrrolidine-2-carboxylic acid (1-benzo[1,3]dioxol-5-yl-1-cyano-methyl)-amide, (S)-1-(5-Phenyl-pentanoyl)-pyrrolidine-2-carboxylic acid [1-(3-chloro-phenyl)-1-cyano-methyl]-amide, (S)-1-(5-Phenyl-pentanoyl)-pyrrolidine-2-carboxylic acid (1-benzo[1,3]dioxol-5-yl-1-cyano-methyl)-amide, (S)-1-[2-(2,4-Dimethyl-phenoxy)-ethanoyl]-pyrrolidine-2-carboxylic acid (1-benzo[1,3]dioxol-5-yl-1-cyano-methyl)-amide, (S)-1-[2-(2-Methoxy-phenoxy)-ethanoyl]-pyrrolidine-2-carboxylic acid (1-benzo[1,3]dioxol-5-yl-1-cyano-methyl)-amide, (S)-1-(3-Cyclohexyl-propanoyl)-pyrrolidine-2-carboxylic acid [1-(3-chloro-phenyl)-1-cyano-methyl]-amide, (S)-1-[2-(3-Methoxy-phenoxy)-ethanoyl]-pyrrolidine-2-carboxylic acid [1-(3-chloro-phenyl)-1-cyano-methyl]-amide, (S)-1-[3-(2,3,4-Trimethoxy-phenyl)-propanoyl]-pyrrolidine-2-carboxylic acid [1-(3-chloro-phenyl)-1-cyano-methyl]-amide, (S)-1-(2-Benzyloxy-ethanoyl)-pyrrolidine-2-carboxylic acid [1-(3-chloro-phenyl)-1-cyano-methyl]-amide, (S)-1-(1-Cyclopropyl-methanoyl)-pyrrolidine-2-carboxylic acid [1-(3-chloro-phenyl)-1-cyano-methyl]-amide, (S)-1-[2-(2-Methoxy-phenoxy)-ethanoyl]-pyrrolidine-2-carboxylic acid [1-(3-chloro -phenyl)-1-cyano-methyl]-amide, (S)-1-(1-Cyclohexyl-methanoyl)-pyrrolidine-2-carboxylic acid [1-cyano-1-(3,4-dimethoxy-phenyl)-methyl]-amide, (S)-1-[2-(4-Ethoxy-phenyl)-ethanoyl]-pyrrolidine-2-carboxylic acid [1-cyano-1-(3,4-dimethoxy-phenyl)-methyl]-amide, (S)-1-[3-(3,4,5-Trimethoxy-phenyl)-propanoyl]-pyrrolidine-2-carboxylic acid [1-(3-chloro-phenyl)-1-cyano-methyl]-amide, (S)-1-(Naphthalene-2-sulfonyl)-pyrrolidine-2-carboxylic acid [1-cyano-1-(3-phenoxy-phenyl)-methyl]-amide, (S)-1-(Naphthalene-2-sulfonyl)-pyrrolidine-2-carboxylic acid (1-benzo[1,3]dioxol-5-yl-1-cyano-methyl)-amide, (S)-1-(3-Cyclopentyl-propanoyl)-pyrrolidine-2-carboxylic acid [1-(3-chloro-phenyl)-1-cyano-methyl]-amide, (S)-1-(3-Cyclopentyl-propanoyl)-pyrrolidine-2-carboxylic acid (1-benzo[1,3]dioxol-5-yl-1-cyano-methyl)-amide, (S)-1-(3-Fluoro-benzylthiocarbamoyl)-pyrrolidine-2-carboxylic acid [1-cyano-1-(3,4-dimethoxy-phenyl)-methyl]-amide, and (S)-1-[2-(2,4-Dimethyl-phenoxy)-ethanoyl]-pyrrolidine-2-carboxylic acid [1-cyano-1-(3,4-dimethoxy-phenyl)-methyl]-amide.

Especially preferred compounds of formula (I) are (S)-2-[(R)-(Cyano-phenyl-methyl)-carbamoyl]-pyrrolidine-1-carboxylic acid benzyl ester, (2S,3R)-2-{(R)- and (S)-[Cyano-(3,4-dimethoxy-phenyl)-methyl]-carbamoyl}-3-methyl-pyrrolidine-1-carboxylic acid benzyl ester, (S)-2-[(R)- and (S)-(Benzo[1,3]dioxol-5-yl-cyano-methyl)-carbamoyl]-pyrrolidine-1-carboxylic acidbenzyl ester, (S)-2-{(R)- and (S)-[(3-Bromo-phenyl)-cyano-methyl]-carbamoyl}-pyrrolidine-1-carboxylic acid benzyl ester, (S)-2-{(R)- and (S)-[(3-Chloro-phenyl)-cyano-methyl]-carbamoyl}-pyrrolidine-1-carboxylic acid benzyl ester, (S)-1-Benzyloxyacetyl-pyrrolidine-2-carboxylic acid ((R)- and (S)-benzo[1,3]dioxol-5-yl-cyano-methyl)-amide, (S)-1-(3-Cyclopentyl-propionyl)-pyrrolidine-2-carboxylic acid ((R)- and (S)-benzo[1,3]dioxol-5-yl-cyano-methyl)-amide, (S)-2-{(R)- and (S)-[(4-Benzyloxy-3-methoxy-phenyl)-cyano-methyl]-carbamoyl}-pyrrolidine-1-carboxylic acid benzyl ester, and (S)-1-[(Furan-2-ylmethyl)-thiocarbamoyl]-pyrrolidine-2-carboxylic acid [(R)- and (S)-cyano-(3,4-dimethoxy-phenyl)-methyl]-amide.

Other especially preferred compounds of formula (I) are (S)-1-[2-(3-Bromo-phenyl)-ethanoyl]-pyrrolidine-2-carboxylic acid (1-benzo[1,3]dioxol-5-yl-1-cyano-methyl)-amide, (S)-1-[2-(3-Bromo-phenyl)-ethanoyl]-pyrrolidine-2-carboxylic acid [1-cyano-1-(3,4-dimethoxy-phenyl)-methyl]-amide, (S)-1-[2-(4-Bromo-phenyl)-ethanoyl]-pyrrolidine-2-carboxylic acid [1-cyano-1-(3,4-dimethoxy-phenyl)-methyl]-amide, (S)-1-[2-(4-Chloro-phenyl)-ethanoyl]-pyrrolidine-2-carboxylic acid [1-(3-chloro-phenyl)-1-cyano-methyl]-amide, (S)-1-[2-(4-Fluoro-phenyl)-ethanoyl]-pyrrolidine-2-carboxylic acid (1-benzo[1,3]dioxol-5-yl-1-cyano-methyl)-amide, (S)-1-[2-(4-Chloro-phenyl)-ethanoyl]-pyrrolidine-2-carboxylic acid [1-cyano-1-(3,4-dimethoxy-phenyl)-methyl]-amide, (S)-1-[2-(4-Fluoro-phenyl)-ethanoyl]-pyrrolidine-2-carboxylic acid [1-cyano-1-(3,4-dimethoxy-phenyl)-methyl]-amide, and (S)-1-[2-(4-Bromo-phenyl)-ethanoyl]-pyrrolidine-2-carboxylic acid (1-benzo[1,3]dioxol-5-yl-1-cyano-methyl)-amide.

Other especially preferred compounds of formula (I) are
(S)-1-(2-o-Tolyloxy-ethanoyl)-pyrrolidine-2-carboxylic acid [1-cyano-1-(3,4-dimethoxy-phenyl)-methyl]-amide, and
(S)-1-(2-o-Tolyloxy-ethanoyl)-pyrrolidine-2-carboxylic acid (1-benzo[1,3]dioxol-5-yl-1-cyano-methyl)-amide.

The invention also relates to compounds of formula (IV)

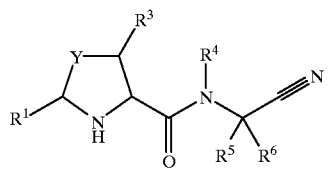

(IV)

wherein Y, $R^1$, $R^3$, $R^4$, $R^5$ and $R^6$ have the same significances as given for compounds of formula (I).

The invention also relates to the use of compounds as defined above for the treatment or prophylaxis of diseases which are associated with cysteine proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease. In a preferred embodiment, the invention relates to the use of compounds as defined above for the treatment or prophylaxis of osteoporosis, instable angina pectoris or plaque rupture.

Further, the invention relates to compounds as defined above for use as therapeutic active substances, in particular in context with diseases which are associated with cysteine proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease. In a preferred embodiment, the invention relates to compounds as defined above for use as therapeutic active substances in context with osteoporosis, instable angina pectoris or plaque rupture.

The invention also relates to pharmaceutical compositions comprising a compound as defined above and a pharmaceutically acceptable carrier and/or adjuvant, in particular for use in context with diseases which are associated with cysteine proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease. In a preferred embodiment, the invention relates to pharmaceutical compositions comprising a compound as defined above and a pharmaceutically acceptable carrier and/or adjuvant for use in context with osteoporosis, instable angina pectoris or plaque rupture.

A further embodiment of the present invention refers to the use of compounds as defined above for the preparation of medicaments for the treatment or prophylaxis of diseases which are associated with cystein proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease. In a preferred embodiment, the invention relates to the use of compounds as defined above for the preparation of medicaments for the treatment or prophylaxis of osteoporosis, instable angina pectoris or plaque rupture. Such medicaments comprise a compound as defined above.

An additional embodiment of the invention relates to a method for the prophylactic and/or therapeutic treatment of disorders in which cathepsin K plays a significant pathological role, such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease, which method comprises administering a compound as defined above to a human being or an animal. A preferred embodiment of the invention relates to a method for the prophylactic and/or therapeutic treatment of osteoporosis, instable angina pectoris or plaque rupture, which method comprises administering a compound as defined above to a human being or an animal.

The invention further relates to a process for the manufacture of compounds of formula (I) which process comprises a) reacting a compound of formula (II)

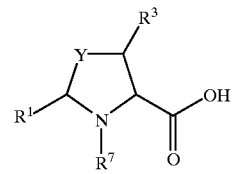

(II)

with a compound of formula (III)

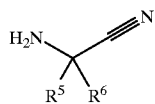

(III)

wherein Y, $R^1$, $R^3$, $R^5$, $R^6$ and $R^7$ have the significances given above, or b) reacting a compound of formula (IV)

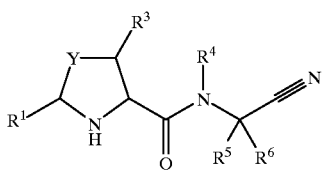

with a compound of formula (V), (VI), (VII) or (VIII)

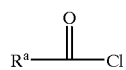

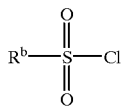

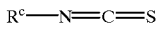

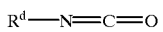

wherein Y, $R^1$, $R^3$, $R^4$, $R^5$, $R^6$, $R^a$, $R^b$, $R^c$ and $R^d$ have the significances given above.

The invention also relates to a process as described above, which process comprises the preparation of pharmaceutically acceptable salts and/or pharmaceutically acceptable esters. The formation of the esters and/or salts can be carried out at different stages of the process, e.g. with the compound of formula (I) or with the corresponding starting materials.

The reaction of a compound of formula (II) with a compound of formula (III) can be carried out by methods known to the person skilled in the art. The reaction can conveniently be carried out by dissolving compound (II), compound (III), TPTU (O-1,2-Dihydro-2-oxo-1-pyridyl)-N, N,N',N'-tetramethyluronium tetrafluoroborate) and H ünigsbase (N-Ethyldiisopropylamine) in MeCN and stirring the mixture at room temperature for 6 to 16 hours. The reaction mixture can be concentrated and the product can be obtained by methods known to the person skilled in the art, e.g. by extraction and column chromatography. Alternatively, a compound of formula (II) can be dissolved in $CH_2Cl_2$ and reacted for 6 to 16 hours at room temperature with a compound of formula (III) in the presence of N-methylmorpholin, HOBT and EDCI. The product can be obtained by, methods known per se, e.g. by extraction and HPLC.

The reaction of a compound of formula (IV) with a compound of formula (V), (VI), (VII) or (VIII) is conveniently carried out by preparing a solution of compound (IV) in $CH_2Cl_2$ and adding a solution of compound (V), (VI) or (VII) in $CH_2Cl_2$. To this mixture, Triethylamin is added and after shaking 6 to 16 hours at room temperature formic acid is added. The product can be isolated and purified by methods known per se, e.g. by evaporation of the solvent and HPLC.

In order to prepare pharmaceutically acceptable salts and/or pharmaceutically acceptable esters of compounds of formula (I), it is possible to prepare the corresponding esters and/or salts starting from the compounds of formula (I). It is also possible, to form the esters and/or salts at an earlier stage, e.g. to form the corresponding salts an/or esters of the corresponding starting materials. The methods to prepare pharmaceutically acceptable salts and/or pharmaceutically acceptable esters as defined before are known in the art.

Compounds of formula (II) are prepared by methods already known to the person skilled in the art. Conveniently, the corresponding amino acid is converted to the corresponding methyl ester by reacting the amino acid in MeOH in the presence of thionylchloride. The resulting intermediate product is isolated by methods known per se, e.g. by extraction and evaporation of the solvent. The intermediate product is linked to the desired substituent $R^7$ analogously to the method described above. The methyl ester is then saponified to yield a compound of formula (II) by dissolving the methyl ester and 2 N NaOH in MeOH and stirring the mixture 5 to 16 hours at room temperature. The resulting compound (II) is isolated by methods known per se, e.g. by extraction and evaporation of the solvent.

Compounds of formula (III) can conveniently be obtained by adding a solution of the corresponding aldehyde in $CH_2Cl_2$ to a solution of $NH_4Cl$ and NaCN in $H_2O$ and MeOH at 0° C. The mixture is stirred and allowed to warm to room temperature. After addition of $NH_3$ solution and completion of the reaction the resulting compound of formula (III) is isolated and purified by methods known to the person skilled in the art, e.g. by extraction. The corresponding hydrochlorid can be prepared by methods known per se.

Chiral compounds of formula (III) can conveniently be obtained by adding ammonia to a mixed anhydride (prepared from a suitable t-BOC protected amino acid and isobutylchloroformate) at −10° C. The reaction mixture is stirred at room temperature for 1–5 h. After completion of the reaction the resulting t-BOC protected amino acid amide is isolated and purified by methods known to the person skilled in the art, e.g. by extraction. The Boc protected amino acid amide and triethylamine are dissolved in THF and trifluoroacetic acid anhydride at 0° C. The mixture is stirred for 1–5 h at 0° C., then at room temperature for 1–2 h. After isolation and purification of the resulting intermediate product, e.g. by evaporation of the solvent and flash chromatography, the t-BOC protective group can be cleaved off with HCl in acetic acid to yield the desired compound of formula (III).

Compounds of formula (IV) can conveniently be obtained by reacting the corresponding t-BOC protected amino acid with a compound of formula (III) analogous to the method described above. After isolation and purification of the resulting intermediate product, e.g. by evaporation of the solvent and flash chromatography, the t-BOC protective group can be cleaved off with trifluoro-acetic acid to yield the desired compound of formula (IV) with trifluoro-acetic acid.

Compounds of formula (V), (VI), (VII) and (VIII) are either commercially available or can be obtained by methods known in the art.

The present invention relates to all compounds of formula (I), as prepared by one of the processes described above.

The inhibitory activity of the compounds against cathepsin K, S, L and B was tested at room temperature in 96-wells opaque white polystyrene plates (Costar). The cathepsin K inhibitory activity was tested as follows:

5 µl of an inhibitor diluted in 5 mM sodium phosphate, NaCl 15 mM pH 7.4 containing 1% DMSO (final concentrations: 10–0.0001 µM) were preincubated for 10 min with 35 µl of human recombinant cathepsin K (final concentration: 1 nM) diluted in assay buffer (100 mM sodium acetate pH 5.5 containing 5 mM EDTA and 20 mM cysteine). After addition of 10 µl of the fluorogenic substrate Z-Leu-Arg- MCA diluted in assay buffer (final concentration: 5 μM), increase of fluorescence (excitation at 390 nm and emission at 460 nm) was measured for 7.5 min every 45 sec. The initial velocity (RFU/min) was derived from the linear fit of the 11 reading points.

The cathepsin B inhibitory activity was assayed under the same conditions as the cathepsin K inhibitory activity using human liver cathepsin B (Calbiochem) at a final concentration of 1 nM.

The cathepsin L inhibitory activity was assayed under the same conditions as the cathepsin K inhibitory activity using human liver cathepsin L (Calbiochem) at a final concentration of 3 nM.

Cathepsin S inhibitory activity was assayed analogously to the cathepsin K inhibitory activity, except that the buffer was 100 mM potassium phosphate, 5 mM EDTA, 5 mM DTT (freshly added), 0.01% Triton X-100, pH 6.5 and the fluorogenic substrate was Z-Val-Val-Arg-MCA (Bachem) (final concentration: 20 μM). Human recombinant cathepsin S (Wiederanders et al., *Eur. J. Biochem.* 1997, 250, 745–750) was used at a final concentration of 0.5 nM.

The results are given as $IC_{50}$ values which denote the concentration of the inhibitor at which the enzymatic activity is inhibited by 50%. The $IC_{50}$ values are determined from a linear regression curve from a logit-log plot.

| Compound no. | Cathepsin K $IC_{50}$ (μMol/l) | Cathepsin S $IC_{50}$ (μMol/l) | Cathepsin L $IC_{50}$ (μMol) | Cathepsin B $IC_{50}$ (μMol/l) |
|---|---|---|---|---|
| (Example 10) | | | | |
| 2 | 0.046 | >10 | >10 | 2.8 |
| 11 | 0.068 | >10 | >10 | 0.6 |
| 9 | 0.014 | >10 | >10 | 9.5 |
| 22 | 0.016 | >10 | >10 | >10 |
| 20 | 0.026 | >10 | >10 | >10 |
| 33 | 0.027 | >10 | >10 | 2.0 |
| 32 | 0.037 | >10 | >10 | 0.6 |
| 28 | 0.045 | >10 | >10 | >10 |
| 14 | 0.064 | >10 | >10 | 6.2 |
| (Example 11) | | | | |
| 1 | 0.015 | >10 | 7.0 | 2.0 |
| 2 | 0.018 | >10 | >10 | 0.6 |
| 10 | 0.026 | >10 | >10 | 4.0 |

It will be appreciated that the compounds of formula (I) in this invention may be derivatised at functional groups to provide derivatives which are capable of conversion back to the parent compounds in vivo.

As mentioned earlier, medicaments containing a compound of formula (I) are also an object of the present invention, as is a process for the manufacture of such medicaments, which process comprises bringing one or more compounds of formula (I) and, if desired, one or more other therapeutically valuable substances into a galenical administration form.

The pharmaceutical compositions may be administered orally, for example in the form of tablets, coated tablets, dragées, hard or soft gelatine capsules, solutions, emulsions or suspensions. Administration can also be carried out rectally, for example using suppositories; locally or percutaneously, for example using ointments, creams, gels or solutions; or parenterally, e.g. intravenously, intramuscularly, subcutaneously, intrathecally or transdermally, using for example injectable solutions. Furthermore, administration can be carried out sublingually or as opthalmological preparations or as an aerosol, for example in the form of a spray.

For the preparation of tablets, coated tablets, dragées or hard gelatine capsules the compounds of the present invention may be admixed with pharmaceutically inert, inorganic or organic excipients. Examples of suitable excipients for tablets, dragées or hard gelatine capsules include lactose, maize starch or derivatives thereof, talc or stearic acid or salts thereof.

Suitable excipients for use with soft gelatine capsules include for example vegetable oils, waxes, fats, semi-solid or liquid polyols etc.; according to the nature of the active ingredients it may however be the case that no excipient is needed at all for soft gelatine capsules.

For the preparation of solutions and syrups, excipients which may be used include for example water, polyols, saccharose, invert sugar and glucose.

For injectable solutions, excipients which may be used include for example water, alcohols, polyols, glycerine, and vegetable oils.

For suppositories, and local or percutaneous application, excipients which may be used include for example natural or hardened oils, waxes, fats and semi-solid or liquid polyols.

The pharmaceutical compositions may also contain preserving agents, solubilising agents, stabilising agents, wetting agents, emulsifiers, sweeteners, colorants, odorants, salts for the variation of osmotic pressure, buffers, coating agents or antioxidants. As mentioned earlier, they may also contain other therapeutically valuable agents.

It is a prerequisite that all adjuvants used in the manufacture of the preparations are non-toxic.

Intravenous, intramuscular or oral administration is a preferred form of use. The dosages in which the compounds of formula (I) are administered in effective amounts depend on the nature of the specific active ingredient, the age and the requirements of the patient and the mode of application. In general, daily dosages of about 1 mg–1000 mg, preferably 5 mg–500 mg, per day come into consideration.

The following Examples shall illustrate preferred embodiments of the present invention but are not intended to limit the scope of the invention. Other compounds of formula (I) can be prepared according to the general methods described above or in analogy to the examples.

EXAMPLE 1

Preparation of (R,S)-α-amino-3-bromophenylacetonitrile

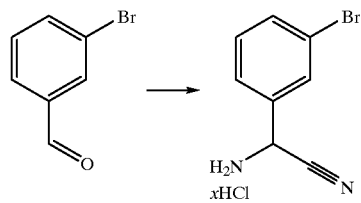

NH$_4$Cl (2.14 g, 40 mmol) and NaCN (1.96 g, 40 mmol) are dissolved in 20 ml H$_2$O and 20 ml MeOH and cooled to 0° C. A solution of 3-bromobenzaldehyde (4.68 ml, 40 mmol) in 15 ml CH$_2$Cl$_2$ and 15 MeOH is added dropwise over 30 min. The mixture is allowed to warm to RT and stirred for 0.5 h. NH$_3$ solution (25% in H$_2$O) (6 ml, 80 mmol) is added. The mixture is stirred for 16 h at RT. The organic solvents are evaporated and H$_2$O is added (5 to 10 ml). The water layer is extracted with CH$_2$Cl$_2$ (2×50 ml) and the latter is washed with H$_2$O (20 ml) and brine (20 ml), dried over Na$_2$SO$_4$ and evaporated. The oily residue is dissolved in 75 ml ether. While stirring vigorously dropwise a 4 M HCl solution in dioxane is added. A solid precipitates and is filtered and dried. To recrystallize the solid is dissolved in as little MeOH as possible (do not heat!). Now, while stirring, ether is added until precipitation has finished. The precipitate is filtered and dried in vacuo.

Yield: 40% MS: 229 (MNH4+)

EXAMPLE 2

Preparation of Chiral amino Nitrites (S)-(Carbamoyl-phenyl-methyl)-carbamic acid tert-butyl ester 25% aqueous ammonia (63 mmol) is added to the mixed anhydride (prepared from 8 mmol (S)-BOC-phenyl glycine and 8 mmol iso-butylchloroformate) at −10° C. The mixture is stirred for 1 h at this temperature, then over night at RT and concentrated. The residue is dissolved in 20 ml ethyl acetate, washed with saturated sodium bicarbonate, 2N HCL, brine dried over sodium sulfate and evaporated.

Yield: 97%, MS: 251 (MH+)

(R)-(Carbamoyl-phenyl-methyl)-carbamic acid tert-butyl ester is prepared analogously to (S)-(Carbamoyl-phenyl-methyl)-carbamic acid tert-butyl ester.

Preparation of (S)-(Cyano-phenyl-methyl)-carbamic acid tert-butyl ester (S)-(Carbamoyl-phenyl-methyl)-carbamic acid tert-butyl ester (1.93 g, 7.7 mmol) and triethylamine (2.4 ml, 17 mmol) are dissolved in THF (40 ml) and trifluoroacetic acid anhydride (1.2 ml, 8.5 mmol) is added at 0° C. The mixture is stirred at 0° C. for 3 h and evaporated. Dichloromethane and water are added. The organic phase is separated, dried over sodium sulfate and evaporated. The crude product is purified by chromatography (silica gel, ethyl acetate/hexane=8:2, $R_f$=0.3).

Yield: 86%, MS: 250 (MH+18)

(R)-(Cyano-phenyl-methyl)-carbamic acid tert-butyl ester is prepared analogously to (S)-(Cyano-phenyl-methyl)-carbamic acid tert-butyl ester Preparation of (S)-Amino-phenyl-acetonitrile hydrochloride (S)-(Cyano-phenyl-methyl)-carbamic acid tert-butyl ester (1.5 g, 6.6 mmol) is dissolved in 30 ml ethyl acetate and 4N HCl in ethyl acetate (33 ml) is added at 0° C. The mixture is stirred at RT for 3 h and evaporated. The product is washed with dietyl ether and dried in vacuo, (silica gel, ethyl acetate, $R_f$=0.7).

Yield: 84%, MS: 151 (MH+18)

(R)-Amino-phenyl-acetonitrile hydrochloride is prepared analogously to (S)-Amino-phenyl-acetonitrile hydrochloride.

EXAMPLE 3

Preparation of (1RS,2RS,5RS)-3-Aza-bicyclo[3.1.0]hexane-2-carboxylic acid methyl ester)

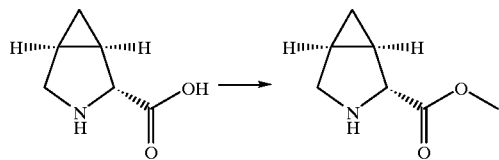

Trans-3-aza-bicyclo[3.1.0]hexane-2-carboxylic acid (0.50 g, 3.54 mmol) is suspended in 15 ml MeOH (under argon) and cooled to 0° C. Thionylchloride (0.28 ml, 3.90 mmol) is added slowly over 10 min. The reaction mixture is refluxed for 2.5 h. The solvent is evaporated leaving an oily residue which is dissolved in CH$_2$Cl$_2$ (20 ml). The organic layer is washed with saturated Na$_2$CO$_3$ (10 ml) and the H$_2$O layer is extracted again with CH$_2$Cl$_2$ (3×20 ml). The collected organic layers are washed with brine (30 ml), dried over Na$_2$—SO$_4$ and evaporated, leaving a yellow oil.

Yield: 98%.

Preparation of trans-3-Benzoyl-3-aza-bicyclo[3.1.0]hexane-2-carboxylic acid methyl ester

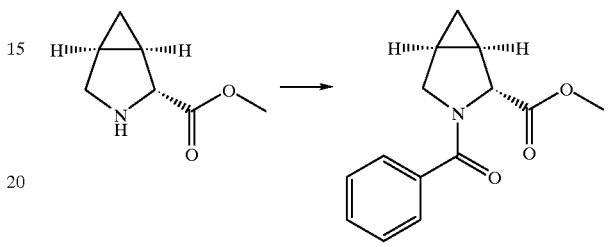

The (1RS, 2RS, 5RS)-3-Aza-bicyclo[3.1.0]hexane-2-carboxylic acid methyl ester (0.55 g, 3.1 mmol) is dissolved in 20 ml CH$_2$Cl$_2$. Benzoylchloride (0.43 ml, 3.7 mmol) and N-methylmorpholine (NMM, 0.75 ml, 6.8 mmol) are added. 4-Dimethylaminopyridine (DMAP, 38 mg, 0.31 mmol) is added. The reaction mixture is stirred at RT for 16 h. The solvent is evaporated leaving an slightly yellow oil which is purified by column chromatography (silica, $R_f$=0.5, ethyl acetate/hexane 1:1).

Yield 52%, MS: 246 (MH+)

Preparation of trans-3-Benzoyl-3-aza-bicyclo[3.1.0]hexane-2-carboxylic acid

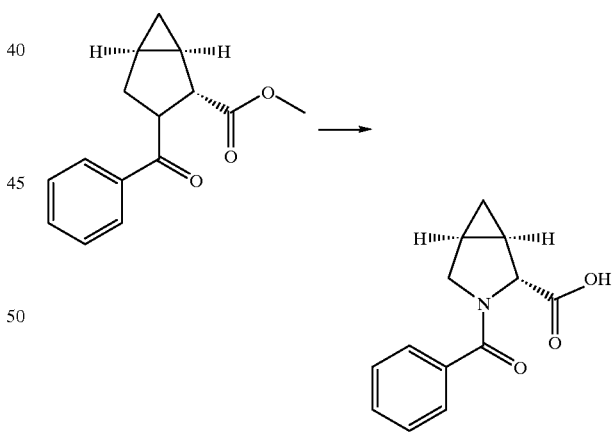

Trans-3-Benzoyl-3-aza-bicyclo[3.1.0]hexane-2-carboxylic acid methyl ester (0.392 g, 1.6 mmol) and 2 N NaOH (1.6 ml, 3.2 mmol) are dissolved in 10 ml MeOH. The mixture is stirred at RT for 6 h. The solution is concentrated, the residue is dissolved in ethyl acetate (30 ml) and extracted with H$_2$O (2×15 ml). The collected H$_2$O layers are neutralized with 2 N HCl and extracted with ethyl acetate (2×20 ml). The collected ethyl acetate layers are washed with brine (30 ml), dried over Na$_2$SO$_4$ and evaporated leaving a white solid which is dried in vacuo.

Yield 90%.

EXAMPLE 4

Preparation of trans-3-Benzoyl-3-aza-bicyclo[3.1.0]hexane-2-carboxylic acid [(3-bromo-phenyl)-cyano-methyl]-amide

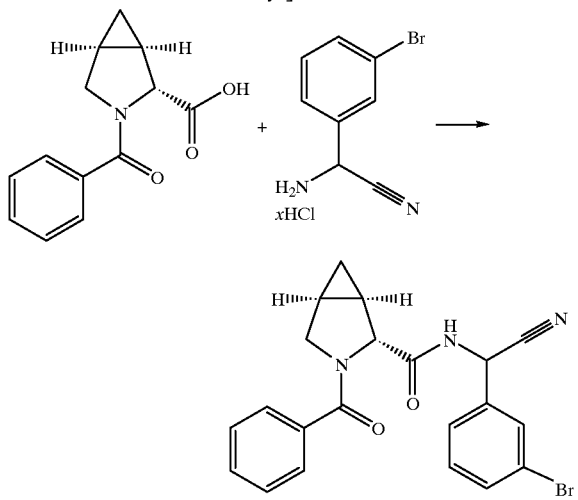

Trans-3-Benzoyl-3-aza-bicyclo[3.1.0]hexane-2-carboxylic acid (0.201 g, 0.87 mmol), DL-α-amino-3-bromophenylacetonitrile (0.215 g, 0.87 mmol), O-1,2-Dihydro-2-oxo-1-pyridyl)-N,N,N',N'-tetramethyluronium tetrafluoroborate (TPTU, 0.258 g, 0.87 mmol) and N-Ethyldiisopropylamine (0.45 ml, 2.61 mmol) are dissolved in 25 ml MeCN. The mixture is stirred at RT for 16 h. The solution is concentrated, the residue is dissolved in ethyl acetate (30 ml) and extracted with $H_2O$ (2×15 ml). The $H_2O$ layers are extracted with ethyl acetate (20 ml). The collected ethyl acetate layers are washed with saturated $NaHCO_3$ (2×20 ml), brine (30 ml), dried over $Na_2SO_4$ and evaporated. The yellow oil is purified by preparative HPLC.

| column: | HP-CombiHT XDB-C18, 21.2 mm I.D. × 50 mm, Series No DN 1020 |
|---|---|
| method: | Flow: 40 ml/min |
| 0 mm | 80% water, 20% acetonitrile |
| 0.2 mm | 80% water, 20% acetonitrile |
| 3.5 mm | 5% water, 95% acetonitrile |
| 4.7 mm | 5% water, 95% acetonitrile |
| 4.8 mm | 80% water, 20% acetonitrile |
| 4.9 mm | 80% water, 20% acetonitrile |
| machine: | Prep HPLC System Dynamax Model SD-1, UV-1 |
| Yield 15 %, MS: 441 (MNH4+) | |

EXAMPLE 5

Preparation of (S)-2-{(R)- and (S)-[(3-Chloro-phenyl)-cyano-methyl]-carbamoyl}-pyrrolidine-1-carboxylic acid benzyl ester (Mixture of epimers, METHOD F)

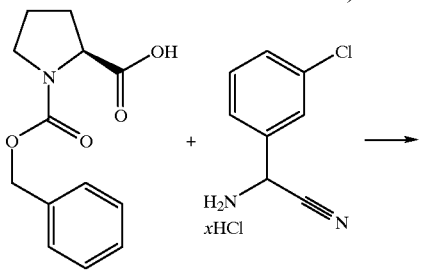

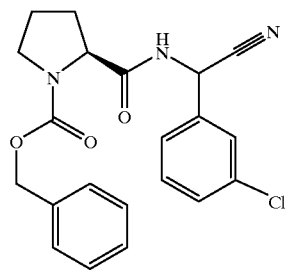

A solution of 0.7 mmol (S)-Pyrrolidine-1,2-dicarboxylic acid 1-benzyl ester (educt 1), 5.2 mmol N-methylmorpholin, 0.15 mmol HOBT and 1.78 mmol EDCI in 12 ml $CH_2Cl_2$ is added to 0.97 mmol (R,S)-Amino-(3-chloro-phenyl)-acetonitrile-hydrochloride (educt 2). After shaking overnight the reaction mixture is extracted with 10 ml 1N HCl and the $CH_2Cl_2$ was evaporated. The compound is purified by HPLC:

| column: | HP-CombiHT XDB-C18, 21.2 mm I.D. × 50 mm, Series No DN 1020 |
|---|---|
| method: | Flow: 40 ml/min |
| 0 mm | 80% water, 20% acetonitrile |
| 0.2 mm | 80% water, 20% acetonitrile |
| 3.5 mm | 5% water, 95% acetonitrile |
| 4.7 mm | 5% water, 95% acetonitrile |
| 4.8 mm | 80% water, 20% acetonitrile |
| 4.9 mm | 80% water, 20% acetonitrile |
| machine: | Prep HPLC System Dynamax Model SD-1, UV-1 |
| Yield: 43%, MS: 396 (M-H) | |

EXAMPLE 6

Preparation of (S)-Pyrrolidine-2-carboxylic acid [(R)- and (S)-cyano-(3-chloro-phenyl)-methyl]amide-trifluoroacetate (Mixture of epimers, METHOD G)

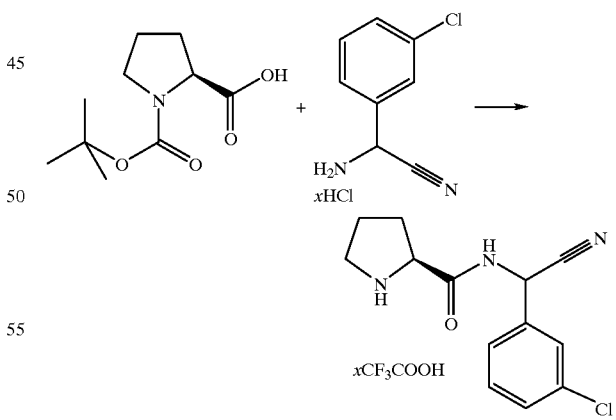

To a solution of 15.7 mmol (S)-Pyrrolidine-1,2-dicarboxylic acid 1-tert.butyl ester, 17.2 mmol (R,S)-Amino-(3-chloro-phenyl)-acetonitrile-hydrochloride, 1.57 mmol HOBT and 18.8 mmol EDCI in 150 ml $CH_2Cl_2$ is added 109.7 mmol N-methylmorpholine. After stirring overnight at RT the reaction mixture is extracted with 150 ml 10% $KHSO_4$ and 150 ml sat. $NaHCO_3$, dried over $MgSO_4$, evaporated and purified by flash chromatography (4 cm Glassfrit, 2 cm silicagel 0.04–0.063, eluent 400 ml $CH_2Cl_2$). BOC-cleavage is performed with 17 ml TFA in 50 ml $CH_2Cl_2$ within 4 hours at RT. Evaporation yields a brown oil which iss used without further purification.

EXAMPLE 7

Preparation of (S)-1-(3-Cyclopentyl-propionyl) pyrrolidine-2-carboxylic acid [(R)- and (S)-(3-chloro-phenyl)-cyano-methyl]-amide (Mixture of epimers, METHOD H)

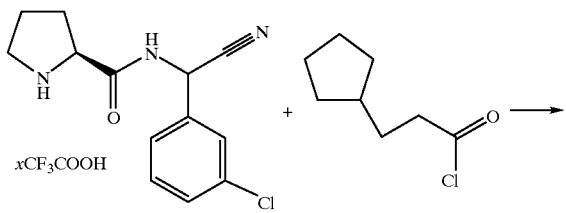

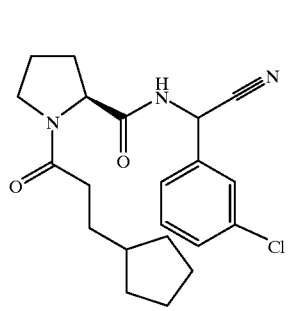

To a solution of 0.17 mmol 1:1mixture of Pyrrolidine-2-carboxylic acid (R)- and (S)-cyano-(3-chloro-phenyl)-methyl-amide-trifluoroacetate (educt 1) in 3 ml $CH_2Cl_2$ is added a solution of 0.187 mmol 3-Cyclopentyl propionyl-chloride (educt 2) in 1 ml $CH_2Cl_2$. To this mixture is added 0.36 mmol triethylamine. After shaking overnight at RT formic acid is added, the $CH_2Cl_2$ is evaporated and the compound purified by HPLC:

| column: | HP-CombiHT XDB-C18, 21.2 mm I.D. × 50 mm, Series No DN 1020 |
|---|---|
| method: | Flow: 40 ml/min |
| 0 mm | 80% water, 20% acetonitrile |
| 0.2 mm | 80% water, 20% acetonitrile |
| 3.5 mm | 5% water, 95% acetonitrile |
| 4.7 mm | 5% water, 95% acetonitrile |
| 4.8 mm | 80% water, 20% acetonitrile |
| 4.9 mm | 80% water, 20% acetonitrile |
| machine: | Prep HPLC System Dynamax Model SD-1, UV-1 |

Yield: 25%, MS: 388 (MH+)

EXAMPLE 8

Preparation of (S)-1-(Naphthalene-1-sulfonyl)-pyrrolidine-2-carboxylic acid [(R)- and (S)-cyano-(3,4-dimethoxy-phenyl)-methyl]-amide (Mixture of epimers, METHOD H)

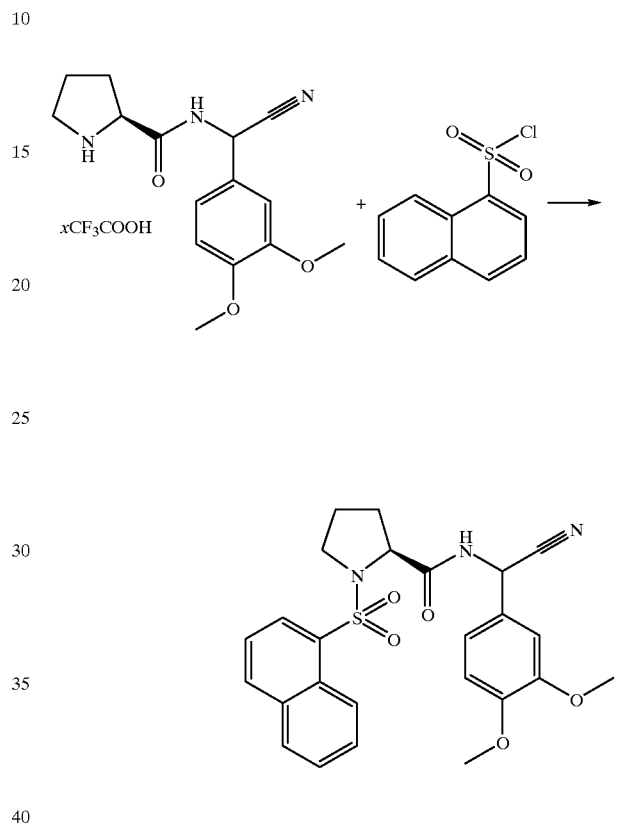

To a solution of 0.17 mmol 1:1 mixture of Pyrrolidine-2-carboxylic acid (R)- and (S)-cyano-(3,4-dimethoxy-phenyl)-methyl]-amide-trifluoroacetate (educt 1) in 3 ml $CH_2Cl_2$ is added a solution of 0.187 mmol Naphthalene-1-sulfonyl chloride (educt 2) in 1 ml $CH_2Cl_2$. To this mixture is added 0.36 mmol triethylamin. After shaking overnight at RT formic acid is added, the $CH_2Cl_2$ is evaporated and the compound purified by HPLC:

| column: | HP-CombiHT XDB-C18, 21.2 mm I.D. × 50 mm, Series No DN 1020 |
|---|---|
| method: | Flow: 40 ml/min |
| 0 mm | 80% water, 20% acetonitrile |
| 0.2 mm | 80% water, 20% acetonitrile |
| 3.5 mm | 5% water, 95% acetonitrile |
| 4.7 mm | 5% water, 95% acetonitrile |
| 4.8 mm | 80% water, 20% acetonitrile |
| 4.9 mm | 80% water, 20% acetonitrile |
| machine: | Prep HPLC System Dynamax Model SD-1, UV-1 |

Yield: 19%, MS: 497 (MNH)

EXAMPLE 9

Preparation of (S)-Pyrrolidine-1,2-dicarboxylic acid 2-{[(R)- and (S)-(3-chloro-phenyl)-cyano-methyl]-amide}1-[(R)-(1-naphthalen-1-yl-ethyl)-amide] (Mixture of epimers, METHOD H)

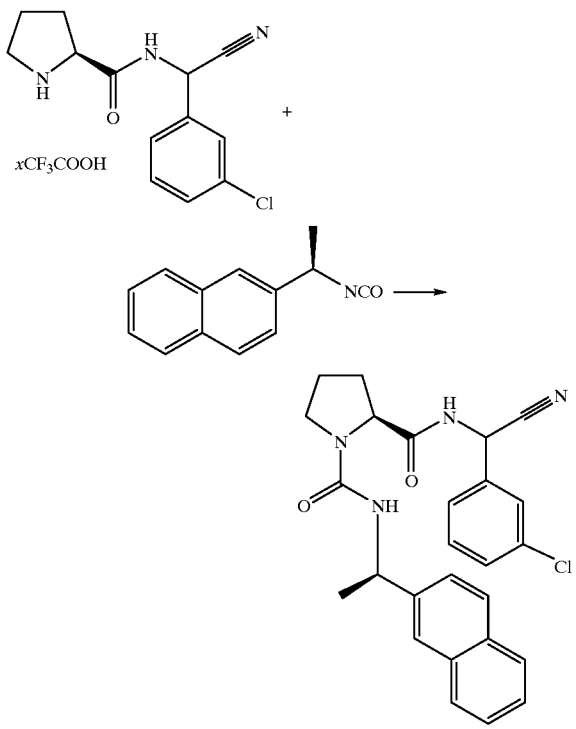

To a solution of 0.17 mmol 1:1 mixture of Pyrrolidine-2-carboxylic acid (R)- and (S)-cyano-(3-chloro-phenyl)-methyl-amide-trifluoroacetate (educt 1) in 3 ml $CH_2Cl_2$ is added a solution of 0.187 mmol (R)-1-(1-Isocyanato-ethyl)-naphthalene (educt 2) in 1 ml $CH_2Cl_2$. To this mixture is added 0.36 mmol triethylamin. After shaking overnight at RT formic acid is added, the $CH_2Cl_2$ is evaporated and the compound purified by HPLC:

| | |
|---|---|
| 4.7 mm | 5% water, 95% acetonitrile |
| 4.8 mm | 80% water, 20% acetonitrile |
| 4.9 mm | 80% water, 20% acetonitrile |
| machine: | Prep HPLC System Dynamax Model SD-1, UV-1 |

Yield: 19%, MS: 461 (MH$^+$)

EXAMPLE 10

Preparation of other compounds of formula (I)

Several additional compounds of formula (I) have been prepared. The following table shows an overview of the products, the educts and the method used for the preparation.

| No. | Compound | Method | Educt 1 | Educt 2 | MS |
|---|---|---|---|---|---|
| 10.1 | (1RS,2RS,5SR)-2-{[(RS)- or -[(SR)-Cyano-(3,4-dimethoxy-phenyl)-methyl]-carbamoyl}-3-aza-bicyclo[3.1.0]hexane-3-carboxylic acid benzyl ester | E | (1RS,2RS,5SR)-3-Aza-bicyclo[3.1.0]hexane-2,3-dicarboxylic acid 3-benzyl ester | (R,S)-Amino-(3,4-dimethoxy-phenyl)-acetonitrile hydrochloride | 453 (MNH$_4^+$) |
| 10.2 | (S)-2-[(R)-(Cyano-phenyl-methyl)-carbamoyl]-pyrrolidine-1-carboxylic acid benzyl ester | E | (S)-Pyrrolidine-1,2-dicarboxylic acid 1-benzyl ester | (R)-Amino-phenyl-acetonitrile hydrochloride | 422 (M-OAc) |
| 10.3 | (S)-2-[(S)-(Cyano-phenyl-methyl)-carbamoyl]-pyrrolidine-1-carboxylic acid benzyl ester | E | (S)-Pyrrolidine-1,2-dicarboxylic acid 1-benzyl ester | (S)-Amino-phenyl-acetonitrile hydrochloride | 422 (M-OAc) |
| 10.4 | (S)-1-(3-methyl-butyryl)-pyrrolidine-2-carboxylic acid (R)- and (S)-(cyano-phenyl-methyl)-amide | E | (S)-1-(3-Methyl-butyryl)-pyrrolidine-2-carboxylic acid | (R,S)-Amino-phenyl-acetonitrile hydrochloride | 331 (MNH$_4^+$) |
| 10.5 | (S)-2-[(S)- and (R)-[Cyano-(3-methoxy-phenyl)-methyl]-carbamoyl}-pyrrolidine-1-carboxylic acid benzyl ester | E | (S)-Pyrrolidine-1,2-dicarboxylic acid 1-benzyl ester | (R,S)-Amino-(3-methoxy-phenyl)-acetonitrile hydrochloride | 394 (MH$^+$) |
| 10.6 | (S)-2-{(S)- and (R)-[(3-Bromo-phenyl)-cyano-methyl]-carbamoyl}-pyrrolidine-1-carboxylic acid benzyl ester | E | (S)-Pyrrolidine-1,2-dicarboxylic acid 1-benzyl ester | (R,S)-Amino-(3-bromo-phenyl)-acetonitrile hydrochloride | 459 (MNH$_4^+$) |
| 10.7 | (S)-2-{(S)- and (R)-[Cyano-(3-hydroxy-phenyl)-methyl]-carbamoyl}-pyrrolidine-1-carboxylic acid benzyl ester | E | (S)-Pyrrolidine-1,2-dicarboxylic acid 1-benzyl ester | (R,S)-Amino-(3-hydroxy-phenyl)-acetonitrile hydrochloride | 378 (M-H) |
| 10.8 | (S)-2-[(R)- and (S)-(Cyano-cyclopropyl-methyl)-carbamoyl]-pyrrolidine-1-carboxylic acid benzyl ester | F | (S)-Pyrrolidine-1,2-dicarboxylic acid 1-benzyl ester | (R,S)-Amino-cyclopropyl-acetonitrile hydrochloride | 350 (MNa$^+$) |
| 10.9 | (S)-2-[(R)- and (S)-(Benzo[1,3]dioxol-5-yl-cyano-methyl)-carbamoyl]-pyrrolidine-1-carboxylic acid benzyl ester | F | (S)-Pyrrolidine-1,2-dicarboxylic acid 1-benzyl ester | (R,S)-Amino-benzo[1,3]dioxol-5-yl-acetonitrile hydrochloride | 425 (MNH$_4^+$) |
| 10.10 | (R)-4-{(R)- and (S)-[Cyano-(3,4-dimethoxy-phenyl)-methyl]-carbamoyl}-thiazolidine-3-carboxylic acid benzyl ester | F | (R)-Thiazolidine-3,4-dicarboxylic acid 3-benzyl ester | (R,S)-Amino-(3,4-dimethoxy-phenyl)-acetonitrile hydrochloride | 464 (MNa$^+$) |

| No. | Compound | Method | Educt 1 | Educt 2 | MS |
|---|---|---|---|---|---|
| 10.11 | (2S,3R)-2-{(R)- and (S)-[Cyano-(3,4-dimethoxy-phenyl)-methyl-carbamoyl}-3-methyl-pyrrolidine-1-carboxylic acid benzyl ester | F | (2S,3R)-3-Methyl-pyrrolidine-1,2-dicarboxylic acid 1-benzyl ester | (R,S)-Amino-(3,4-dimethoxy-phenyl)-acetonitrile hydrochloride | 438 (MH$^+$) |
| 10.12 | (S)-1-Benzylthiocarbamoyl-pyrrolidine-2-carboxylic acid ((R)- and (S)-benzo[1,3]dioxol-5-yl-cyano-methyl)-amide | H | Pyrrolidine-2-carboxylic acid ((R)- and (S)-benzo[1,3]dioxol-5-yl-cyano-methyl)-amide; compound with trifluoro-acetic acid | Benzylisothiocyanate | 423 (MH$^+$) |
| 10.13 | (S)-1-Benzylthiocarbamoyl-pyrrolidine-2-carboxylic acid [(R)- and (S)-cyano-(3,4-dimethoxy-phenyl)-methyl]-amide | H | Pyrrolidine-2-carboxylic acid [(R)- and (S)-cyano-(3,4-dimethoxy-phenyl)-methyl]-amide; compound with trifluoro-acetic acid | Benzylisothiocyanate | 439 (MH$^+$) |
| 10.14 | (S)-1-[(Furan-2-ylmethyl)-thiocarbamoyl]-pyrrolidine-2-carboxylic acid [(R)- and (S)-cyano-(3,4-dimethoxy-phenyl)-methyl]-amide | H | Pyrrolidine-2-carboxylic acid [(R)- and (S)-cyano-(3,4-dimethoxy-phenyl)-methyl]-amide; compound with trifluoro-acetic acid | 2-Isothiocyanatomethyl-furan | 429 (MH$^+$) |
| 10.15 | (S)-1-Benzylthiocarbamoyl-pyrrolidine-2-carboxylic acid [(R)- and (S)-(3-chloro-phenyl)-cyano-methyl]-amide | H | Pyrrolidine-2-carboxylic acid [(R)- and (S)-(3-chloro-phenyl)-cyano-methyl]-amide; compound with trifluoro-acetic acid | Benzylisothiocyanate | 412 (MH$^+$) |
| 10.16 | (S)-1-(3-Fluoro-benzylthiocarbamoyl)-pyrrolidine-2-carboxylic acid [(R)- and (S)-(3-chloro-phenyl)-cyano-methyl]-amide | H | Pyrrolidine-2-carboxylic acid [(R)- and (S)-(3-chloro-phenyl)-cyano-methyl]-amide; compound with trifluoro-acetic acid | 3-Fluoro benzylisothiocyanate | 431 (MH$^+$) |
| 10.17 | (S)-2-((R)- and (S)-1-Cyano-3-phenyl-propylcarbamoyl)-pyrrolidine-1-carboxylic acid benzyl ester | F | (S)-Pyrrolidine-1,2-dicarboxylic acid 1-benzyl ester | (R,S)-2-Amino-4-phenyl-butyronitrile hydrochloride | 392 (MH$^+$) |
| 10.18 | (R)-4-{(R)- and (S)-[(4-Chloro-phenyl)-cyano-methyl]-carbamoyl}-thiazolidine-3-carboxylic acid benzyl ester | F | (R)-Thiazolidine-3,4-dicarboxylic acid 3-benzyl ester | (R,S)-Amino-(4-chloro-phenyl)-acetonitrile hydrochloride | 416 (MH$^+$) |
| 10.19 | (S)-2-{(R)- and (S)-[(3-Chloro-phenyl)-cyano-methyl]-carbamoyl}-pyrrolidine-1-carboxylic acid benzyl ester | F | (S)-Pyrrolidine-1,2-dicarboxylic acid 1-benzyl ester | (R,S)-Amino-(3-chloro-phenyl)-acetonitrile hydrochloride | 396 (MH$^+$) |
| 10.20 | (S)-2-[(R)- and (S)-(Cyano-o-tolyl-methyl)-carbamoyl]-pyrrolidine-1-carboxylic acid benzyl ester | F | (S)-Pyrrolidine-1,2-dicarboxylic acid 1-benzyl ester | (R,S)-Amino-(2-methyl-phenyl)-acetonitrile hydrochloride | 378 (MH$^+$) |
| 10.21 | (S)-2-{(R)- and (S)-[Cyano-(2,4-dimethoxy-phenyl)-methyl]-carbamoyl}-pyrrolidine-1-carboxylic acid benzyl ester | F | (S)-Pyrrolidine-1,2-dicarboxylic acid 1-benzyl ester | (R,S)-Amino-(2,4-dimethoxy-phenyl)-acetonitrile hydrochloride | 422 (M-H) |
| 10.22 | (S)-2-{(R)- and (S)-[(3-Bromo-phenyl)-cyano-methyl]-carbamoyl}-pyrrolidine-1-carboxylic acid benzyl ester | F | (S)-Pyrrolidine-1,2-dicarboxylic acid 1-benzyl ester | (R,S)-Amino-(3-bromo-phenyl)-acetonitrile hydrochloride | 442 (M-H) |
| 10.23 | (S)-2-{(R)- and (S)-[Cyano-(3-fluoro-phenyl)-methyl]-carbamoyl}-pyrrolidine-1-carboxylic acid benzyl ester | F | (S)-Pyrrolidine-1,2-dicarboxylic acid 1-benzyl ester | (R,S)-Amino-(3-fluoro-phenyl)-acetonitrile hydrochloride | 380 (M-H) |
| 10.24 | (S)-2-[(R)- and (S)-(Cyano-m-tolyl-methyl)-carbamoyl]-pyrrolidine-1-carboxylic acid benzyl ester | F | (S)-Pyrrolidine-1,2-dicarboxylic acid 1-benzyl ester | (R,S)-Amino-(3-methyl-phenyl)-acetonitrile hydrochloride | 376 (M-H) |
| 10.25 | (S)-2-{(R)- and (S)-[(4-Bromo-phenyl)-cyano-methyl]-carbamoyl}-pyrrolidine-1-carboxylic acid benzyl ester | F | (S)-Pyrrolidine-1,2-dicarboxylic acid 1-benzyl ester | (R,S)-Amino-(4-bromo-phenyl)-acetonitrile hydrochloride | 442 (M-H) |
| 10.26 | (S)-2-{(R)- and (S)-[Cyano-(3,4,5-trimethoxy-phenyl)-methyl]-carbamoyl}-pyrrolidine-1-carboxylic acid benzyl ester | F | (S)-Pyrrolidine-1,2-dicarboxylic acid 1-benzyl ester | (R,S)-Amino-(3,4,5-trimethoxy-phenyl)-acetonitrile hydrochloride | 452 (M-H) |
| 10.27 | (S)-2-{(R)- and (S)-[Cyano-(3-phenoxy-phenyl)-methyl]-carbamoyl}-pyrrolidine-1-carboxylic acid benzyl ester | F | (S)-Pyrrolidine-1,2-dicarboxylic acid 1-benzyl ester | (R,S)-Amino-(3-phenoxy-phenyl)-acetonitrile hydrochloride | 454 (M-H) |
| 10.28 | (S)-2-{(R)- and (S)-[(4-Benzyloxy-3-methoxy-phenyl)-cyano-methyl]-carbamoyl}-pyrrolidine-1-carboxylic acid benzyl ester | F | (S)-Pyrrolidine-1,2-dicarboxylic acid 1-benzyl ester | (R,S)-Amino-(4-benzyloxy-3-methoxy-phenyl)-acetonitrile hydrochloride | 498 (M-H) |
| 10.30 | (S)-1-(Naphthalene-2-sulfonyl)-pyrrolidine-2-carboxylic acid [(R)- and (S)-cyano-(3,4-dimethoxy-phenyl)-methyl]-amide | H | Pyrrolidine-2-carboxylic acid [(R)- and (S)-cyano-(3,4-dimethoxy-phenyl)-methyl]-amide; compound with trifluoro-acetic acid | Naphthalene-2-sulfonyl chloride | 480 (MH$^+$) |
| 10.31 | (S)-1-(Naphthalene-1-sulfonyl)-pyrrolidine-2-carboxylic acid ((R)- and (S)-benzo[1,3]dioxol-5-yl-cyano-methyl)-amide | H | Pyrrolidine-2-carboxylic acid ((R)- and (S)-benzo[1,3]dioxol-5-yl-cyano-methyl)-amide; compound with trifluoro-acetic acid | Naphthalene-1-sulfonyl chloride | 481 (MH$^+$) |

-continued

| No. | Compound | Method | Educt 1 | Educt 2 | MS |
|---|---|---|---|---|---|
| 10.32 | (S)-1-(3-Cyclopentyl-propionyl)-pyrrolidine-2-carboxylic acid ((R)- and (S)-benzo[1,3]dioxol-5-yl-cyano-methyl)-amide | H | Pyrrolidine-2-carboxylic acid ((R)- and (S)-benzo[1,3]dioxol-5-yl-cyano-methyl)-amide; compound with trifluoro-acetic acid | Cyclopentyl-propionyl chloride | 398 (MH$^+$) |
| 10.33 | (S)-1-Benzyloxyacetyl-pyrrolidine-2-carboxylic acid ((R)- and (S)-benzo[1,3]dioxol-5-yl-cyano-methyl)-amide | H | Pyrrolidine-2-carboxylic acid ((R)- and (S)-benzo[1,3]dioxol-5-yl-cyano-methyl)-amide; compound with trifluoro-acetic acid | Benzyloxy-acetyl chloride | 422 (MH$^+$) |
| 10.34 | (S)-1-(5-Dimethylamino-naphthalene-1-sulfonyl)-pyrrolidine-2-carboxylic acid [(R)- and (S)-cyano-(3,4-dimethoxy-phenyl)-methyl]-amide | H | Pyrrolidine-2-carboxylic acid [(R)- and (S)-cyano-(3,4-dimethoxy-phenyl)-methyl]-amide; compound with trifluoro-acetic acid | 5-Dimethylamino-naphthalene-1-sulfonyl chloride | 523 (MH$^+$) |
| 10.35 | (S)-1-(Naphthalene-1-sulfonyl)-pyrrolidine-2-carboxylic acid [(R)- and (S)-cyano-(3,4-dimethoxy-phenyl)-methyl]-amide | H | Pyrrolidine-2-carboxylic acid [(R)- and (S)-cyano-(3,4-dimethoxy-phenyl)-methyl]-amide; compound with trifluoro-acetic acid | Naphthalene-1-sulfonyl chloride | 497 (MNH$_4^+$) |
| 10.36 | (S)-1-(Naphthalene-2-carbonyl)-pyrrolidine-2-carboxylic acid [(R)- and (S)-cyano-(3,4-dimethoxy-phenyl)-methyl]-amide | H | Pyrrolidine-2-carboxylic acid [(R)- and (S)-cyano-(3,4-dimethoxy-phenyl)-methyl]-amide; compound with trifluoro-acetic acid | Naphthalene-2-carbonyl chloride | 444 (MH$^+$) |
| 10.37 | (S)-1-(Naphthalene-1-carbonyl)-pyrrolidine-2-carboxylic acid [(R)- and (S)-cyano-(3,4-dimethoxy-phenyl)-methyl]-amide | H | Pyrrolidine-2-carboxylic acid [(R)- and (S)-cyano-(3,4-dimethoxy-phenyl)-methyl]-amide; compound with trifluoro-acetic acid | Naphthalene-1-carbonyl chloride | 444 (MH$^+$) |
| 10.38 | (S)-1-(3-Cyclopentyl-propionyl)-pyrrolidine-2-carboxylic acid [(R)- and (S)-cyano-(3,4-dimethoxy-phenyl)-methyl]-amide | H | Pyrrolidine-2-carboxylic acid [(R)- and (S)-cyano-(3,4-dimethoxy-phenyl)-methyl]-amide; compound with trifluoro-acetic acid | Cyclopentyl-propionyl chloride | 414 (MH$^+$) |
| 10.39 | (S)-1-Benzyloxyacetyl-pyrrolidine-2-carboxylic acid [(R)- and (S)-cyano-(3,4-dimethoxy-phenyl)-methyl]-amide | H | Pyrrolidine-2-carboxylic acid [(R)- and (S)-cyano-(3,4-dimethoxy-phenyl)-methyl]-amide; compound with trifluoro-acetic acid | Benzyloxyacetyl chloride | 438 (MH$^+$) |
| 10.40 | (S)-1-(Naphthalene-1-carbonyl)-pyrrolidine-2-carboxylic acid [(R)- and (S)-(3-chloro-phenyl)-cyano-methyl]-amide | H | Pyrrolidine-2-carboxylic acid [(R)- and (S)-(3-chloro-phenyl)-cyano-methyl]-amide; compound with trifluoro-acetic acid | Naphthalene-1-carbonyl chloride | 418 (MH$^+$) |
| 10.41 | (S)-1-(3-Cyclopentyl-propionyl)-pyrrolidine-2-carboxylic acid [(R)- and (S)-(3-chloro-phenyl)-cyano-methyl]-amide | H | Pyrrolidine-2-carboxylic acid [(R)- and (S)-(3-chloro-phenyl)-cyano-methyl]-amide; compound with trifluoro-acetic acid | Cyclopentyl-propionyl chloride | 388 (MH$^+$) |
| 10.42 | (S)-1-Phenylacetyl-pyrrolidine-2-carboxylic acid [(R)- and (S)-(3-chloro-phenyl)-cyano-methyl]-amide | H | Pyrrolidine-2-carboxylic acid [(R)- and (S)-(3-chloro-phenyl)-cyano-methyl]-amide; compound with trifluoro-acetic acid | Phenylacetyl chloride | 382 (MH$^+$) |
| 10.43 | (S)-1-Benzyloxyacetyl-pyrrolidine-2-carboxylic acid [(R)- and (S)-(3-chloro-phenyl)-cyano-methyl]-amide | H | Pyrrolidine-2-carboxylic acid [(R)- and (S)-(3-chloro-phenyl)-cyano-methyl]-amide; compound with trifluoro-acetic acid | Benzyloxyacetyl chloride | 412 (MH$^+$) |
| 10.44 | (S)-Pyrrolidine-1,2-dicarboxylic acid 2-{[(R)- and (S)-(3-chloro-phenyl)-cyano-methyl]-amide}1-[(R)-(1-naphthalen-1-yl-ethyl)-amide] | H | Pyrrolidine-2-carboxylic acid [(R)- and (S)-(3-chloro-phenyl)-cyano-methyl]-amide; compound with trifluoro-acetic acid | (R)-1-(1-Isocyanato-ethyl)-naphthalene | 461 (MH$^+$) |
| 10.45 | (S)-1-(Naphthalene-1-carbonyl)-pyrrolidine-2-carboxylic acid [(R)- and (S)-(3-bromo-phenyl)-cyano-methyl]-amide | H | (S)-Pyrrolidine-2-carboxylic acid [(R)- and (S)-3-bromo-phenyl)-cyano-methyl]-amide; compound with trifluoro-acetic acid | Naphthalene-1-carbonyl chloride | 462 (MH$^+$) |
| 10.46 | (S)-1-Phenylacetyl-pyrrolidine-2-carboxylic acid [(R)- and (S)-(3-bromo-phenyl)-cyano-methyl]-amide | H | (S)-Pyrrolidine-2-carboxylic acid [(R)- and (S)-3-bromo-phenyl)-cyano-methyl]-amide; compound with trifluoro-acetic acid | Phenylacetyl chloride | 426 (MH$^+$) |

-continued

| No. | Compound | Method | Educt 1 | Educt 2 | MS |
|---|---|---|---|---|---|
| 10.47 | (S)-1-Benzyloxyacetyl-pyrrolidine-2-carboxylic acid [(R)- and (S)-(3-bromo-phenyl)-cyano-methyl]-amide | H | (S)-Pyrrolidine-2-carboxylic acid [(R)- and (S)-3-bromo-phenyl)-cyano-methyl]-amide; compound with trifluoro-acetic acid | Benzyloxyacetyl chloride | 456 (MH$^+$) |
| 10.48 | (S)-Pyrrolidine-1,2-dicarboxylic acid 2-{[(R)- and (S)-(3-bromo-phenyl)-cyano-methyl]-amide}1-[(R)-(1-naphthalen-1-yl-ethyl)-amide] | H | (S)-Pyrrolidine-2-carboxylic acid [(R)- and (S)-3-bromo-phenyl)-cyano-methyl]-amide; compound with trifluoro-acetic acid | (R)-1-(l-Isocyanato-ethyl)-naphthalene | 507 (MH$^+$) |
| 10.49 | (S)-1-(3-Cyclopentyl-propionyl)-pyrrolidine-2-carboxylic acid [(R)- and (S)-cyano-(3-methoxy-phenyl)-methyl]-amide | H | Pyrrolidine-2-carboxylic acid [(R)- and (S)-cyano-(3-methoxy-phenyl)-methyl]-amide; compound with trifluoro-acetic acid | Cyclopentyl-propionyl chloride | 384 (MH$^+$) |
| 10.50 | (S)-1-Phenylacetyl-pyrrolidine-2-carboxylic acid [(R)- and (S)-cyano-(3-methoxy-phenyl)-methyl]-amide | H | Pyrrolidine-2-carboxylic acid [(R)- and (S)-cyano-(3 methoxy-phenyl)-methyl]-amide; compound with trifluoro-acetic acid | Phenylacetyl chloride | 378 (MH$^+$) |
| 10.51 | (S)-1-Benzyloxyacetyl-pyrrolidine-2-carboxylic acid [(R)- and (S)-cyano-(3-methoxy-phenyl)-methyl]-amide | H | Pyrrolidine-2-carboxylic acid [(R)- and (S)-cyano-(3-methoxy-phenyl)-methyl]-amide; compound with trifluoro-acetic acid | Benzyloxyacetyl chloride | 408 (MH$^+$) |
| 10.52 | 2-((R)- and (S)-1-Cyano-3-phenyl-propylcarbamoyl)-pyrrolidine-1-carboxylic acid benzyl ester | F | (S)-Pyrrolidine-1,2-dicarboxylic acid 1-benzyl ester | (R,S)-2-Amino-4-phenyl-butyronitrile hydrochloride | 392 (MH$^+$) |
| 10.53 | (S)-2-{[(R)- and (S)-Cyano-(3-methoxy-phenyl)-methyl]-carbamoyl}-pyrrolidine-1-carboxylic acid benzyl ester | F | (S)-Pyrrolidine-1,2-dicarboxylic acid 1-benzyl ester | (R,S)-Amino-(3-methoxy-phenyl)-acetonitrile hydrochloride | 394 (MH$^+$) |
| 10.54 | (S)-2-{(R)- and (S)-[Cyano-(3,4-dimethoxy-phenyl)-methyl]-carbamoyl}-pyrrolidine-1-carboxylic acid benzyl ester | F | (S)-Pyrrolidine-1,2-dicarboxylic acid 1-benzyl ester | (R,S)-Amino-(3,4-dimethoxy-phenyl)-acetonitrile hydrochloride | 441 (MH$^+$) |
| 10.55 | (S)-1-(2-Phenyl-ethenesulfonyl)-pyrrolidine-2-carboxylic acid ((R)- and (S)-benzo[1,3]dioxol-5-yl-cyano-methyl)-amide | H | Pyrrolidine-2-carboxylic acid ((R)- and (S)-benzo[1,3]dioxol-5-yl-cyano-methyl)-amide; compound with trifluoro-acetic acid | Phenyl-ethenesulfonyl chloride | 440 (MH$^+$) |
| 10.56 | (S)-Pyrrolidine-1,2-dicarboxylic acid 2-{(R)- and (S)-[cyano-(3,4-dimethoxy-phenyl)-methyl]-amide}1-[(S)-(1-naphthalen-1-yl-ethyl)-amide] | H | Pyrrolidine-2-carboxylic acid [(R)- and (S)-cyano-(3,4-dimethoxy-phenyl)-methyl]-amide; compound with trifluoro-acetic acid | (S)-1-(1-Isocyanato-ethyl)-naphthalene | 487(MH$^+$) |
| 10.57 | (S)-1-(2-Phenyl-ethenesulfonyl)-pyrrolidine-2-carboxylic acid [(R)- and (S)-cyano-(3,4-dimethoxy-phenyl)-methyl]-amide | H | Pyrrolidine-2-carboxylic acid [(R)- and (S)-cyano-(3,4-dimethoxy-phenyl)-methyl]-amide; compound with trifluoro-acetic acid | Phenyl-ethenesulfonyl chloride | 456 (MH$^+$) |

The following methods were used:

METHOD E

Coupling of Protected Amino Acids with Amino Nitrites

The protected amino acid, the amino nitrile, TPTU (O-1,2-Dihydro-2-oxo-1-pyridyl)-N,N,N',N'-tetramethyluronium tetrafluoroborate) and Hünigsbase (N-Ethyldiisopropyl-amine) are dissolved in MeCN. The mixture is stirred at RT for 6–16 h. The solution is concentrated and the residue is dissolved in ethyl acetate and extracted with H$_2$O. The H$_2$O layers are extracted with ethyl acetate. The combined ethyl acetate layers are washed NaHCO$_3$, brine, dried over Na$_2$SO$_4$ and evaporated. The crude product is purified by column chromatography.

Yield 60–90%.

METHOD F

Z-AS+Amino Nitrile

A solution of 1 eq (S)-Pyrrolidine-1,2-dicarboxylic acid 1-benzyl ester, 7 eq N-methylmorpholin, 0.2 eq HOBT and 2.4 eq EDCI in 7 ml CH$_2$Cl$_2$ is added to 1.1–1.3 eq amino nitrile-HCl. After shaking overnight the reaction mixture is extracted with 1N HCl and the CH$_2$Cl$_2$ is evaporated. The compounds are purified by HPLC:

| | |
|---|---|
| column: | HP-CombiHT XDB-C18, 21.2 mm I.D. × 50 mm, Series No DN 1020 |
| method: | Flow: 40 ml/min |
| 0 mm | 80% water, 20% acetonitrile |
| 0.2 mm | 80% water, 20% acetonitrile |
| 3.5 mm | 5% water, 95% acetonitrile |
| 4.7 mm | 5% water, 95% acetonitrile |
| 4.8 mm | 80% water, 20% acetonitrile |
| 4.9 mm | 80% water, 20% acetonitrile |
| machine: | Prep HPLC System Dynamax Model SD-1, UV-1 |

METHOD H

Amino Acid Nitrile (Educt 1)+(Educt 2)

Crude 1:1 mixture of Pyrrolidine-2-carboxylic -amide-trifluoroacetate (educt 1)+a.

Carbonylchloride (educt 2) or b. sulfonylchloride (educt 2) or c. Isothiocyanate (educt 2)+triethylamine To a solution of leq Pyrrolidine-2-carboxylic acid amide-TFA (educt 1) in $CH_2Cl_2$ is added a solution of 1.1 eq carbonylchloride (educt 2) or sulfonylchloride (educt 2) or isothiocyanate (educt 2) in $CH_2Cl_2$. To this mixture is added 2.1 eq triethylamine. After shaking overnight at RT formic acid is added, $CH_2Cl_2$ is evaporated and the compound purified by HPLC:

| column: | HP-CombiHT XDB-C18, 21.2 mm I.D. × 50 mm, Series No DN 1020 |
|---|---|
| method: | Flow: 40 ml/min |
| 0 mm | 80% water, 20% acetonitrile |
| 0.2 mm | 80% water, 20% acetonitrile |
| 3.5 mm | 5% water, 95% acetonitrile |
| 4.7 mm | 5% water, 95% acetonitrile |
| 4.8 mm | 80% water, 20% acetonitrile |
| 4.9 mm | 80% water, 20% acetonitrile |
| machine: | Prep HPLC System Dynamax Model SD-1, UV-1 |

EXAMPLE 11
Preparation of other compounds of formula (I)

The following compounds of formula (I) have been prepared from the corresponding educts in analogy to example 10, method H.

| No. | Compound | Educt 1 | Educt 2 | MS |
|---|---|---|---|---|
| 11.1 | (S)-1-[2-(3-Bromo-phenyl)-ethanoyl]-pyrrolidine-2-carboxylic acid (1-benzo[1,3]dioxol-5-yl-1-cyano-methyl)-amide | Pyrrolidine-2-carboxylic acid ((R)- and (S)-benzo[1,3]dioxol-5-yl-cyano-methyl)-amide; compound with trifluoro-acetic acid | 3-Bromophenylacetyl chloride | 471 ($MH^+$) |
| 11.2 | (S)-1-[2-(3-Bromo-phenyl)-ethanoyl]-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | 3-Bromophenylacetyl chloride | 487 ($MH^+$) |
| 11.3 | (S)-1-[2-(4-Bromo-phenyl)-ethanoyl]-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | 4-Bromophenylacetyl chloride | 487 ($MH^+$) |
| 11.4 | (S)-1-[2-(4-Chloro-phenyl)-ethanoyl]-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | 4-Chlorophenylacetyl chloride | 417 ($MH^+$) |
| 11.5 | (S)-1-[2-(4-Fluoro-phenyl)-ethanoyl]-pyrrolidine-2-carboxylic acid (1-benzo[1,3]dioxol-5-yl-1-cyano-methyl)-amide | Pyrrolidine-2-carboxylic acid ((R)- and (S)-benzo[1,3]dioxol-5-yl-cyano-methyl)-amide; compound with trifluoro-acetic acid | 4-Fluorophenylacetyl chloride | 410 ($MH^+$) |
| 11.6 | (S)-1-[2-(4-Chloro-phenyl)-ethanoyl]-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | 4-Chlorophenylacetyl chloride | 442 ($MH^+$) |
| 11.7 | (S)-1-(2-o-Tolyloxy-ethanoyl)-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | (2-Methylphenoxy)acetyl chloride | 438 ($MH^+$) |
| 11.8 | (S)-1-(2-o-Tolyloxy-ethanoyl)-pyrrolidine-2-carboxylic acid (1-benzo[1,3]dioxol-5-yl-1-cyano-methyl)-amide | Pyrrolidine-2-carboxylic acid ((R)- and (S)-benzo[1,3]dioxol-5-yl-cyano-methyl)-amide; compound with trifluoro-acetic acid | (2-Methylphenoxy)acetyl chloride | 422 ($MH^+$) |
| 11.9 | (S)-1-[2-(4-Fluoro-phenyl)-ethanoyl]-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | 4-Fluorophenylacetyl chloride | 426 ($MH^+$) |
| 11.10 | (S)-1-[2-(4-Bromo-phenyl)-ethanoyl]-pyrrolidine-2-carboxylic acid (1-benzo[1,3]dioxol-5-yl-1-cyano-methyl)-amide | Pyrrolidine-2-carboxylic acid ((R)- and (S)-benzo[1,3]dioxol-5-yl-cyano-methyl)-amide; compound with trifluoro-acetic acid | 4-Bromophenylacetyl chloride | 471 ($MH^+$) |
| 11.11 | (S)-1-[2-(4-Bromo-phenyl)-ethanoyl]-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | 4-Bromophenylacetyl chloride | 461 ($MH^+$) |
| 11.12 | (S)-1-[2-(4-Iodo-phenyl)-ethanoyl]-pyrrolidine-2-carboxylic acid (1-benzo[1,3]dioxol-5-yl-1-cyano-methyl)-amide | Pyrrolidine-2-carboxylic acid ((R)- and (S)-benzo[1,3]dioxol-5-yl-cyano-methyl)-amide; compound with trifluoro-acetic acid | 4-Iodophenylacetyl chloride | 518 ($MH^+$) |
| 11.13 | (S)-1-[2-(4-Fluoro-phenyl)-ethanoyl]-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | 4-Fluorophenylacetyl chloride | 400 ($MH^+$) |
| 11.14 | (S)-1-(4-Phenyl-butanoyl)-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | Phenylbutyric chloride | 436 ($MH^+$) |

| No. | Compound | Educt 1 | Educt 2 | MS |
|---|---|---|---|---|
| 11.15 | (S)-1-[2-(3-Bromo-phenyl)-ethanoyl]-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | 3-Bromophenylacetyl chloride | 461 (MH+) |
| 11.16 | (S)-1-(2-Benzo[1,3]dioxol-5-yl-ethanoyl)-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | 3,4-(Methylendioxy)phenylacetyl chloride | 426 (MH+) |
| 11.17 | (S)-1-(2-Phenoxy-ethanoyl)-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | Phenoxyacetyl chloride | 424 (MH+) |
| 11.18 | (S)-1-(2-o-Tolyloxy-ethanoyl)-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | (2-Methylphenoxy)acetyl chloride | 412 (MH+) |
| 11.19 | (S)-1-(2-Benzo[1,3]dioxol-5-yl-ethanoyl)-pyrrolidine-2-carboxylic acid (1-benzo[1,3]dioxol-5-yl-1-cyano-methyl)-amide | Pyrrolidine-2-carboxylic acid ((R)- and (S)-benzo[1,3]dioxol-5-yl-cyano-methyl)-amide; compound with trifluoro-acetic acid | 3,4-(Methylendioxy)phenylacetyl chloride | 436 (MH+) |
| 11.20 | (S)-1-(2-Phenoxy-ethanoyl)-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | Phenoxyacetyl chloride | 398 (MH+) |
| 11.21 | (S)-1-(2-Phenyl-ethanoyl)-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | Phenylacetyl chloride | 382 (MH+) |
| 11.22 | (S)-1-[2-(4-Fluoro-phenoxy)-ethanoyl]-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | (4-Fluorophenoxy)acetyl chloride | 442 (MH+) |
| 11.23 | (S)-1-(2-Benzo[1,3]dioxol-5-yl-ethanoyl)-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | 3,4-(Methylendioxy)phenylacetyl chloride | 452 (MH+) |
| 11.24 | (S)-1-(3-Phenyl-propanoyl)-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | Phenylpropionyl chloride | 422 (MH+) |
| 11.25 | (S)-1-[4-(3,4-Dimethoxy-phenyl)-butanoyl]-pyrrolidine-2-carboxylic acid (1-benzo[1,3]dioxol-5-yl-1-cyano-methyl)-amide | Pyrrolidine-2-carboxylic acid ((R)- and (S)-benzo[1,3]dioxol-5-yl-cyano-methyl)-amide; compound with trifluoro-acetic acid | (3,4-Methoxyphenyl)butyryl chloride | 480 (MH+) |
| 11.26 | (S)-1-[4-(3,4-Dimethoxy-phenyl)-butanoyl]-pyrrolidine-2-carboxylic acid [1-(3-chloro-phenyl)-cyano-methyl]-amide | Pyrrolidine-2-carboxylic acid [(R)- and (S)-(3-chloro-phenyl)-cyano-methyl]-amide; compound with trifluoro-acetic acid | (3,4-Methoxyphenyl)butyryl chloride | 470 (MH+) |
| 11.27 | (S)-1-[2-(4-Iodo-phenyl)-ethanoyl]-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | 4-Iodophenylacetyl chloride | 534 (MH+) |
| 11.28 | (S)-1-[4-(3,4-Dimethoxy-phenyl)-butanoyl]-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | (3,4-Methoxyphenyl)butyryl chloride | 496 (MH+) |
| 11.29 | (S)-1-(3-1H-Indol-3-yl-propanoyl)-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | 3-Indolepropionic acid chloride | 461 (MH+) |
| 11.30 | (S)-1-(4-Phenyl-butanoyl)-pyrrolidine-2-carboxylic acid (1-benzo[1,3]dioxol-5-yl-1-cyano-methyl)-amide | Pyrrolidine-2-carboxylic acid ((R)- and (S)-benzo[1,3]dioxol-5-yl-cyano-methyl)-amide; compound with trifluoro-acetic acid | Phenylbutyryl chloride | 420 (MH+) |
| 11.31 | (S)-1-(2-Phenylsulfanyl-ethanoyl)-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | (Phenylthio)acetyl chloride | 414 (MH+) |
| 11.32 | (S)-1-(4-Cyclohexyl-butanoyl)-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | Cyclohexanebutyric acid chloride | 442 (MH+) |
| 11.33 | (S)-1-(3-Cyclohexyl-propanoyl)-pyrrolidine-2-carboxylic acid (1-benzo[1,3]dioxol-5-yl-1-cyano-methyl)-amide | Pyrrolidine-2-carboxylic acid ((R)- and (S)-benzo[1,3]dioxol-5-yl-cyano-methyl)-amide; compound with trifluoro-acetic acid | Cyclohexanepropionic acid chloride | 412 (MH+) |
| 11.34 | (S)-1-[4-(4-Nitro-phenyl)-butanoyl]-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | (4-Nitrobenzene)butyryl chloride | 481 (MH+) |
| 11.35 | (S)-1-[2-(4-Iodo-phenyl)-ethanoyl]-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | 4-Iodophenylacetyl chloride | 508 (MH+) |

-continued

| No. | Compound | Educt 1 | Educt 2 | MS |
|---|---|---|---|---|
| 11.36 | (S)-1-[2-(2,4-Dimethyl-phenoxy)-ethanoyl]-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | (2,4-Dimethylphenoxy)acetyl chloride | 426 (MH+) |
| 11.37 | (S)-1-[4-(4-Nitro-phenyl)-butanoyl]-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | (4-Nitrobenzene)butyryl chloride | 455 (MH+) |
| 11.38 | (S)-1-(1-Naphthalen-1-yl-methanoyl)-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | 2-Naphthoyl chloride | 418 (MH+) |
| 11.39 | (S)-1-[2-(4-Methoxy-phenoxy)-ethanoyl]-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | (4-Methoxylphenoxy)acetyl chloride | 428 (MH+) |
| 11.40 | (S)-1-(2-Phenyl-ethanoyl)-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | Phenylacetyl chloride | 408 (MH+) |
| 11.41 | (S)-1-[2-(2-Methoxy-phenoxy)-ethanoyl]-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | (2-Methoxylphenoxy)acetyl chloride | 454 (MH+) |
| 11.42 | (S)-1-[2-(4-Methoxy-phenoxy)-ethanoyl]-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | (4-Methoxylphenoxy)acetyl chloride | 454 (MH+) |
| 11.43 | (S)-1-(4-Cyclohexyl-butanoyl)-pyrrolidine-2-carboxylic acid (1-benzo[1,3]dioxol-5-yl-1-cyano-methyl)-amide | Pyrrolidine-2-carboxylic acid ((R)- and (S)-benzo[1,3]dioxol-5-yl-cyano-methyl)-amide; compound with trifluoro-acetic acid | Cyclohexanebutyric acid chloride | 426 (MH+) |
| 11.44 | (S)-1-{1-[1-(4-Chloro-phenyl)-cyclopentyl]-methanoyl}-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | 1-(4-Chlorophenyl)-1-cyclopentanecarboxylic acid chloride | 497 (MH+) |
| 11.45 | (S)-1-((Z)-3-Phenyl-allanoyl)-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | Cinnamoyl chloride | 420 (MH+) |
| 11.46 | (S)-1-(2-Phenylsulfanyl-ethanoyl)-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | (Phenylthio)acetyl chloride | 440 (MH+) |
| 11.47 | (S)-1-[2-(4-Fluoro-phenoxy)-ethanoyl]-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | (4-Fluorophenoxy)acetyl chloride | 416 (MH+) |
| 11.48 | (S)-1-[2-(3-Methoxy-phenoxy)-ethanoyl]-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | (3-Methoxylphenoxy)acetyl chloride | 454 (MH+) |
| 11.49 | (S)-1-(4-Phenyl-butanoyl)-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | 4-Phenylbutyryl chloride | 410 (MH+) |
| 11.50 | (S)-1-[2-(3,4,5-Trimethoxy-phenyl)-ethanoyl]-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | 3,4,5-Trimethoxyphenylacetyl chloride | 472 (MH+) |
| 11.51 | (S)-1-(5-Phenyl-pentanoyl)-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | 4-Phenylpentanoicacid chloride | 450 (MH+) |
| 11.52 | (S)-1-(l-Cyclopropyl-methanoyl)-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | Cyclopropanecarboxylicacid chloride | 358 (MH+) |
| 11.53 | (S)-1-[2-(4-Fluoro-phenoxy)-ethanoyl]-pyrrolidine-2-carboxylic acid (1-benzo[1,3]dioxol-5-yl-1-cyano-methyl)-amide | Pyrrolidine-2-carboxylic acid ((R)- and (S)-benzo[1,3]dioxol-5-yl-cyano-methyl)-amide; compound with trifluoro-acetic acid | (4-Fluorophenoxy)acetyl chloride | 426 (MH+) |
| 11.54 | (S)-1-[2-(4-Chloro-phenoxy)-ethanoyl]-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | (4-Chlorophenoxy)acetyl chloride | 433 (MH+) |
| 11.55 | (S)-1-(2-Phenyl-ethanoyl)-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | Phenylacetyl chloride | 382 (MH+) |

-continued

| No. | Compound | Educt 1 | Educt 2 | MS |
|---|---|---|---|---|
| 11.56 | (S)-1-(3,3-Diphenyl-propanoyl)-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | 3,3-Diphenylpropionicacid chloride | 498 (MH+) |
| 11.57 | (S)-1-[2-(3-Methoxy-phenoxy)-ethanoyl]-pyrrolidine-2-carboxylic acid (1-benzo[1,3]dioxol-5-yl-1-cyano-methyl)-amide | Pyrrolidine-2-carboxylic acid ((R)- and (S)-benzo[1,3]dioxol-5-yl-cyano-methyl)-amide; compound with trifluoro-acetic acid | (3-Methoxylphenoxy)acetyl chloride | 438 (MH+) |
| 11.58 | (S)-1-[2-(4-Ethoxy-phenyl)-ethanoyl]-pyrrolidine-2-carboxylic acid (1-benzo[1,3]dioxol-5-yl-1-cyano-methyl)-amide | Pyrrolidine-2-carboxylic acid ((R)- and (S)-benzo[1,3]dioxol-5-yl-cyano-methyl)-amide; compound with trifluoro-acetic acid | (4-Ethoxyphenyl)acetyl chloride | 436 (MH+) |
| 11.59 | (S)-1-(5-Phenyl-pentanoyl)-pyrrolidine-2-carboxylic acid [1-(3-chloro-phenyl)-1-cyano-methyl]-amide | Pyrrolidine-2-carboxylic acid ((R)- and (S)-(3-chloro-phenyl)-cyano-methyl]-amide; compound with trifluoro-acetic acid | 4-Phenylpentanoicacid chloride | 424 (MH+) |
| 11.60 | (S)-1-(5-Phenyl-pentanoyl)-pyrrolidine-2-carboxylic acid (1-benzo[1,3]dioxol-5-yl-1-cyano-methyl)-amide | Pyrrolidine-2-carboxylic acid ((R)- and (S)-benzo[1,3]dioxol-5-yl-cyano-methyl)-amide; compound with trifluoro-acetic acid | 4-Phenylpentanoicacid chloride | 434 (MH+) |
| 11.61 | (S)-1-[2-(2,4-Dimethyl-phenoxy)-ethanoyl]-pyrrolidine-2-carboxylic acid (1-benzo[1,3]dioxol-5-yl-1-cyano-methyl)-amide | Pyrrolidine-2-carboxylic acid ((R)- and (S)-benzo[1,3]dioxol-5-yl-cyano-methyl)-amide; compound with trifluoro-acetic acid | (2,3-Dimethylphenoxy)acetyl chloride | 436 (MH+) |
| 11.62 | (S)-1-[2-(2-Methoxy-phenoxy)-ethanoyl]-pyrrolidine-2-carboxylic acid (1-benzo[1,3]dioxol-5-yl-1-cyano-methyl)-amide | Pyrrolidine-2-carboxylic acid ((R)- and (S)-benzo[1,3]dioxol-5-yl-cyano-methyl)-amide; compound with trifluoro-acetic acid | (2-Methoxylphenoxy)acetyl chloride | 438 (MH+) |
| 11.63 | (S)-1-(3-Cyclohexyl-propanoyl)-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | Cyclohexylpropionicacid chloride | 402 (MH+) |
| 11.64 | (S)-1-[2-(3-Methoxy-phenoxy)-ethanoyl]-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | (3-Methoxylphenoxy)acetyl chloride | 428 (MH+) |
| 11.65 | (S)-1-[3-(2,3,4-Trimethoxy-phenyl)-propanoyl]-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | 2,3,4-Trimethoxyphenylpropionyl chloride | 486 (MH+) |
| 11.66 | (S)-1-(2-Benzyloxy-ethanoyl)-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | Benzyloxyacetyl chloride | 412 (MH+) |
| 11.67 | (S)-1-(l-Cyclopropyl-methanoyl)-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | Cyclopropanecarboxylicacid chloride | 332 (MH+) |
| 11.68 | (S)-1-[2-(2-Methoxy-phenoxy)-ethanoyl]-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | (2-Methoxylphenoxy)acetyl chloride | 428 (MH+) |
| 11.69 | (S)-1-(1-Cyclohexyl-methanoyl)-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | Cyclohexanecarboxylicacid chloride | 400 (MH+) |
| 11.70 | (S)-1-[2-(4-Ethoxy-phenyl)-ethanoyl]-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | (4-Ethoxyphenyl)acetyl chloride | 452 (MH+) |
| 11.71 | (S)-1-[3-(3,4,5-Trimethoxy-phenyl)-propanoyl]-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | 3,4,5-Trimethoxyphenylpropionyl chloride | 486 (MH+) |
| 11.72 | (S)-1-(Naphthalene-2-sulfonyl)-pyrrolidine-2-carboxylic acid [1-cyano-1-(3-phenoxy-phenyl)-methyl]-amide | (S)-Pyrrolidine-2-carboxylic acid [1-cyano-1-(3-phenoxy-phenyl)-methyl]-amide | Naphthalene-2-sulfonyl chloride | 512 (MH+) |
| 11.73 | (S)-1-(Naphthalene-2-sulfonyl)-pyrrolidine-2-carboxylic acid (1-benzo[1,3]dioxol-5-yl-1-cyano-methyl)-amide | Pyrrolidine-2-carboxylic acid ((R)- and (S)-benzo[1,3]dioxol-5-yl-cyano-methyl)-amide; compound with trifluoro-acetic acid | Naphthalene-2-sulfonyl chloride | 464 (MH+) |
| 11.74 | (S)-1-(3-Cyclopentyl-propanoyl)-pyrrolidine-2-carboxylic acid [1-(3-chloro-phenyl)-1-cyano-methyl]-amide | Pyrrolidine-2-carboxylic acid [(R)- and (S)-(3-chloro-phenyl)-cyano-methyl]-amide; compound with trifluoro-acetic acid | Cyclopentylpropionicacid chloride | 388 (MH+) |
| 11.75 | (S)-1-(3-Cyclopentyl-propanoyl)-pyrrolidine-2-carboxylic acid (1-benzo[1,3]dioxol-5-yl-1-cyano-methyl)-amide | Pyrrolidine-2-carboxylic acid ((R)- and (S)-benzo[1,3]dioxol-5-yl-cyano-methyl)-amide; compound with trifluoro-acetic acid | Cyclopentylpropionicacid chloride | 398 (MH+) |

-continued

| No. | Compound | Educt 1 | Educt 2 | MS |
|---|---|---|---|---|
| 11.76 | (S)-1-(3-Fluoro-benzylthiocarbamoyl)-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | 3-(Fluorobenzyl)isothiocyanate | 457 (MH$^+$) |
| 11.77 | (S)-1-[2-(2,4-Dimethyl-phenoxy)-ethanoyl]-pyrrolidine-2-carboxylic acid [1-cyano-1-(3,4-dimethoxy-phenyl)-methyl]-amide | Pyrrolidine-2-carboxylic acid [(R)- and (S)-cyano-(3,4-dimethoxy-phenyl)-methyl]-amide; compound with trifluoro-acetic acid | (2,4-Dimethylphenoxy)acetyl chloride | 452 (MH$^+$) |

EXAMPLE A

Tablets containing the following ingredients can be manufactured in a conventional manner:

| Ingredients | Per tablet |
|---|---|
| Compound of formula I | 10.0–100.0 mg |
| Lactose | 125.0 mg |
| Maize starch | 75.0 mg |
| Talc | 4.0 mg |
| Magnesium stearate | 1.0 mg |

EXAMPLE B

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

EXAMPLE C

Injection solutions can have the following composition:

| | |
|---|---|
| Compound of formula I | 3.0 mg |
| Gelatine | 150.0 mg |
| Phenol | 4.7 mg |
| Water for injection solutions | ad 1.0 ml |

Upon reading the present specification various alternative embodiments will become obvious to the skilled artisan. These variations are to be considered within the scope and spirit of the subject application which is only to be limited to the claims that follow and their equivalents.

What is claimed is:

1. A compound of the formula:

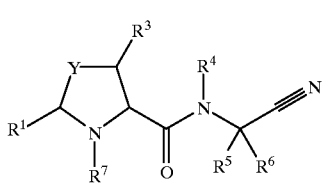

(I)

wherein
Y is CH—R$^2$;
R$^1$ and R$^3$ are each independently hydrogen or methyl and R$^2$ is hydrogen, or R$^1$ is hydrogen and R$^2$ and R$^3$ together are —CH$_2$— thus forming a cyclopropyl ring;

R$^4$, R$^5$ are each independently hydrogen or lower-alkyl;
R$^6$ is cycloalkyl, aryl, aryl-lower-alkyl, heteroaryl, or heteroaryl-lower-alkyl;
R$^7$ is —CO—R$^a$, —SO$_2$—R$^b$ or —CS—NH—R$^c$, wherein
R$^a$ is lower-alkyl, cycloalkyl, cycloalkyl-lower-alkyl, cycloalkyl-lower-alkoxy, aryl, heteroaryl, aryl-lower-alkyl, aryl-lower-alkoxy, heteroaryl-lower-alkoxy, aryl-lower-alkoxy-lower-alkyl, aryloxy-lower-alkyl, arylthio-lower-alkyl, aryl-lower-alkenyl, aryl-cycloalkyl, or R$^d$—NH,
R$^b$ is lower-alkyl, cycloalkyl, cycloalkyl-lower-alkyl, aryl, heteroaryl, aryl-lower-alkyl, or aryl-lower-alkenyl,
R$^c$ is lower-alkyl, cycloalkyl, cycloalkyl-lower-alkyl, aryl, heteroaryl, aryl-lower-alkyl, or heteroaryl-lower-alkyl,
R$^d$ is aryl-lower-alkyl;
or a pharmaceutically acceptable salt or ester thereof.

2. The compound according to claim 1, wherein
R$^7$ is —CO—R$^a$, —SO$_2$—R$^b$ or —CS—NH—R$^c$, wherein
R$^a$ is lower-alkyl, cycloalkyl, cycloalkyl-lower-alkyl, cycloalkyl-lower-alkoxy, aryl, heteroaryl, aryl-lower-alkyl, aryl-lower-alkoxy, heteroaryl-lower-alkoxy, aryl-lower-alkoxy-lower-alkyl, or R$^d$—NH,
R$^b$ is lower-alkyl, cycloalkyl, cycloalkyl-lower-alkyl, aryl, heteroaryl, aryl-lower-alkyl, or aryl-lower-alkenyl,
R$^c$ is lower-alkyl, cycloalkyl, cycloalkyl-lower-alkyl, aryl, heteroaryl, aryl-lower-alkyl, or heteroaryl-lower-alkyl, and
R$^d$ is aryl-lower-alkyl.

3. The compound according to claim 1, wherein the compound is of the formula:

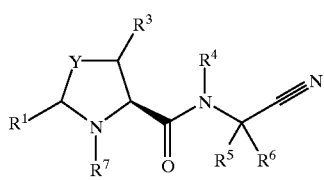

(Ia)

wherein Y, R$^1$, R$^3$, R$^4$, R$^5$, R$^6$ and R$^7$ are as defined in claim 1.

4. The compound according to claim 1, wherein R$^2$ is hydrogen.

5. The compound according to claim 1, wherein R$^1$ is hydrogen.

6. The compound according to claim 1, wherein R$^3$ is hydrogen.

7. The compound according to claim 1, wherein $R^4$ is hydrogen.

8. The compound according to claim 1, wherein $R^5$ is hydrogen.

9. The compound according to claim 1, wherein $R^6$ is phenyl; furanyl; thiophenyl; pyrrolyl; phenyl substituted with alkyl, halogen, hydroxy, alkoxy, —O—$(CH_2)_{1-7}$—O—, aryloxy, or aryl-alkoxy; furanyl substituted with alkyl, halogen, hydroxy, alkoxy, —O—$(CH_2)_{1-7}$—O—, aryloxy, or aryl-alkoxy; thiophenyl substituted with alkyl, halogen, hydroxy, alkoxy, —O—$(CH_2)_{1-7}$—O—, aryloxy, or aryl-alkoxy; or pyrrolyl that is substituted with alkyl, halogen, hydroxy, alkoxy, —O—$(CH_2)_{1-7}$—O—, aryloxy, or aryl-alkoxy.

10. The compound according claim 9, wherein $R^6$ is phenyl, phenyl substituted in meta-position, phenyl substituted in meta- and in para-position, or benzo[1,3]dioxol-5-yl.

11. The compound according to claims 10, wherein $R^6$ is 3-methoxy-phenyl, 3,4-dimethoxy-phenyl, 4-benzyloxy-3-methoxy-phenyl, 3-chloro-phenyl, 3-bromo-phenyl, or benzo[1,3]dioxol-5-yl.

12. The compound according to claim 1, wherein $R^7$ is —CO—$R^a$ and $R^a$ is as defined in claim 1.

13. The compound according to claim 12, wherein $R^a$ is benzyloxy, cyclopentyl-ethylene, or benzyloxy-methylene.

14. The compound according to claim 12, wherein $R^a$ is 3-bromobenzyl, 4-bromobenzyl, 4-chlorobenzyl, 4-fluorobenzyl, or 2-methyl-phenyloxymethylene.

15. The compound according to claim 1, wherein $R^7$ is —CS—NH—$R^c$ and $R^c$ is as defined in claim 1.

16. The compound according to claim 15, wherein $R^c$ is benzyl, 3-fluorobenzyl, or furan-2-yl-methylene.

17. The compounds according to claim 1, wherein $R^7$ is —$SO_2$—$R^b$ and $R^b$ is as defined in claim 1.

18. The compound according to claim 17, wherein $R^b$ is naphthyl.

19. A compound of the formula:

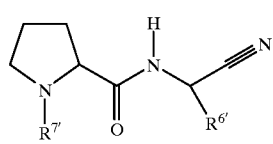

(I')

wherein
$R^{6'}$ is aryl;
$R^{7'}$ is —CO—$R^{a'}$ or —CS—NH—$R^{c'}$, wherein
$R^{a'}$ is cycloalkyl-lower-alkyl, aryl-lower-alkyl, aryl-lower-alkoxy, aryl-lower-alkoxy-lower-alkyl, aryloxy-lower-alkyl, and
$R^{c'}$ is heteroaryl-lower-alkyl;
or a pharmaceutically acceptable salt or ester thereof.

20. The compound of claim 19, wherein $R^{7'}$ is —CO—$R^{a'}$.

21. The compound of claim 20, wherein $R^{a'}$ is cycloalkyl-lower-alkyl.

22. The compound of claim 21, wherein $R^{a'}$ is cyclopentyl-ethyl.

23. The compound of claim 22, wherein $R^{6'}$ is benzo[1,3]dioxol-5-yl.

24. The compound of claim 23, which is (S)-1-(3-cyclopentyl-propionyl)-pyrrolidine-2-carboxylic acid ((R)- and (S)-benzo[1,3]dioxol-5-yl-cyano-methyl)-amide.

25. The compound of claim 20, wherein $R^{a'}$ is aryl-lower-alkoxy.

26. The compound of claim 25, wherein $R^{a'}$ is phenyl-methoxy.

27. The compound of claim 26, wherein $R^{6'}$ is 4-benzyloxy-3-methoxy-phenyl.

28. The compound of claim 27, which is (S)-2-{(R)- and (S)-[(4-benzyloxy-3-methoxy-phenyl)-cyano-methyl]-carbamoyl}-pyrrolidine-1-carboxylic acid benzyl ester.

29. The compound of claim 26, wherein $R^{6'}$ is 3-bromophenyl.

30. The compound of claim 29, which is (S)-2-{(R)- and (S)-[(3-bromo-phenyl)-cyano-methyl]-carbamoyl}-pyrrolidine-1-carboxylic acid benzyl ester.

31. The compound of claim 26, wherein $R^{6'}$ is 3-chlorophenyl.

32. The compound of claim 31, which is (S)-2-{(R)- and (S)-[(3-chloro-phenyl)-cyano-methyl]-carbamoyl}-pyrrolidine-1-carboxylic acid benzyl ester.

33. The compound of claim 26, wherein $R^{6'}$ is phenyl.

34. The compound of claim 33, which is (S)-2-[(R)-(cyano-phenyl-methyl)-carbamoyl]-pyrrolidine-1-carboxylic acid benzyl ester.

35. The compound of claim 26, wherein $R^{6'}$ is benzo[1,3]dioxol-5-yl.

36. The compound of claim 35, which is (S)-2-[(R)- and (S)-(benzo[1,3]dioxol-5-yl-cyano-methyl)-carbamoyl]-pyrrolidine-1-carboxylic acid benzyl ester.

37. The compound of claim 26, wherein $R^{6'}$ is 3,4-dimethoxy-phenyl.

38. The compound of claim 37, which is (2S,3R)-2-{(R)- and (S)-[cyano-(3,4-dimethoxy-phenyl)-methyl]-carbamoyl}-3-methyl-pyrrolidine-1-carboxylic acid benzyl ester.

39. The compound of claim 20, wherein $R^{a'}$ is o-tolyloxy.

40. The compound of claim 39, wherein $R^{6'}$ is 3,4-dimethoxy-phenyl.

41. The compound of claim 40, which is (S)-1-(2-o-tolyloxy-ethanoyl)-pyrrolidine-2-carboxylic acid [1-cyano-1-(3,4-dimethoxy-phenyl)-methyl]-amide.

42. The compound of claim 39, wherein $R^{6'}$ is benzo[1,3]dioxol-5-yl.

43. The compound of claim 42, which is (S)-1-(2-o-tolyloxy-ethanoyl)-pyrrolidine-2-carboxylic acid (1-benzo[1,3]dioxol-5-yl-1-cyano-methyl)-amide.

44. The compound of claim 20, wherein $R^{a'}$ is bromo-phenyl-methyl.

45. The compound of claim 44, wherein $R^{a'}$ is 3-bromo-phenyl-methyl.

46. The compound of claim 45, wherein $R^{6'}$ is benzo[1,3]dioxol-5-yl.

47. The compound of claim 46, which is (S)-1-[2-(3-bromo-phenyl)-ethanoyl]-pyrrolidine-2-carboxylic acid (1-benzo[1,3]dioxol-5-yl-1-cyano-methyl)-amide.

48. The compound of claim 45, wherein $R^{6'}$ is 3,4-dimethoxy-phenyl.

49. The compound of claim 48, which is (S)-1-[2-(3-bromo-phenyl)-ethanoyl]-pyrrolidine-2-carboxylic acid [1-cyano-1-(3,4-dimethoxy-phenyl)-methyl]-amide.

50. The compound of claim 44, wherein $R^{a'}$ is 4-bromo-phenyl-methyl.

51. The compound of claim 50, wherein $R^{6'}$ is 3,4-dimethoxy-phenyl.

52. The compound of claim 51, which is (S)-1-[2-(4-bromo-phenyl)-ethanoyl]-pyrrolidine-2-carboxylic acid [1-cyano-1-(3,4-dimethoxy-phenyl)-methyl]-amide.

53. The compound of claim 50, wherein $R^{6'}$ is benzo[1,3]dioxol-5-yl.

54. The compound of claim 53, which is (S)-1-[2-(4-bromo-phenyl)-ethanoyl]-pyrrolidine-2-carboxylic acid (1-benzo[1,3]dioxol-5-yl-1-cyano-methyl)-amide.

55. The compound of claim 20, wherein R$^{a'}$ is chlorophenyl-methyl.

56. The compound of claim 55, wherein R$^{a'}$ is 4-chlorophenyl-methyl.

57. The compound of claim 56, wherein R$^{6'}$ is 3-chlorophenyl.

58. The compound of claim 57, which is (S)-1-[2-(4-chloro-phenyl)-ethanoyl]-pyrrolidine-2-carboxylic acid [1-(3-chloro-phenyl)-1-cyano-methyl]-amide.

59. The compound of claim 56, wherein R$^{6'}$ is 3,4-dimethoxy-phenyl.

60. The compound of claim 59, which is (S)-1-[2-(4-chloro-phenyl)-ethanoyl]-pyrrolidine-2-carboxylic acid [1-cyano-1-(3,4-dimethoxy-phenyl)-methyl]-amide.

61. The compound of claim 20, wherein R$^{a'}$ is fluorophenyl-methyl.

62. The compound of claim 61, wherein R$^{a'}$ is 4-fluorophenyl-methyl.

63. The compound of claim 62, wherein R$^{6'}$ is 3,4-dimethoxy-phenyl.

64. The compound of claim 63, which is (S)-1-[2-(4-fluoro-phenyl)-ethanoyl]-pyrrolidine-2-carboxylic acid [1-cyano-1-(3,4-dimethoxy-phenyl)-methyl]-amide.

65. The compound of claim 62, wherein R$^{6'}$ is benzo[1,3]dioxol-5-yl.

66. The compound of claim 65, which is (S)-1-[2-(4-fluoro-phenyl)-ethanoyl]-pyrrolidine-2-carboxylic acid (1-benzo[1,3]dioxol-5-yl-1-cyano-methyl)-amide.

67. The compound of claim 20, wherein R$^{a'}$ is aryl-lower-alkoxy-alkyl.

68. The compound of claim 67, wherein R$^{a'}$ is phenyl-methoxy-methyl.

69. The compound of claim 48, wherein R$^{6'}$ is benzo[1,3]dioxol-5-yl.

70. The compound of claim 69, which is (S)-1-benzyloxyacetyl-pyrrolidine-2-carboxylic acid ((R)- and (S)-benzo[1,3]dioxol-5-yl-cyano-methyl)-amide.

71. The compound of claim 19, wherein R$^{7'}$ is —CS—NH—R$^{c'}$.

72. The compound of claim 71, wherein R$^{c'}$ is furan-2yl-methyl.

73. The compound of claim 72, which is (S)-1-[(furan-2-ylmethyl)-thiocarbamoyl]-pyrrolidine-2-carboxylic acid [(R)- and (S)-cyano-(3,4-dimethoxy-phenyl)-methyl]-amide.

74. A compound of the formula:

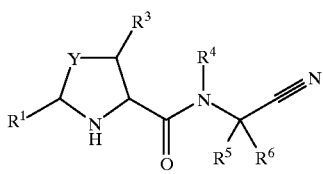

(IV)

wherein

Y is CH—R$^2$;

R$^1$ and R$^3$ are each independently hydrogen or methyl and R$^2$ hydrogen, or R$^1$ is hydrogen and R$^2$ and R$^3$ together are —CH$_2$— thus forming a cyclopropyl ring;

R$^4$, R$^5$ are each independently hydrogen or lower-alkyl;

R$^6$ is cycloalkyl, aryl, aryl-lower-alkyl, heteroaryl, or heteroaryl-lower-alkyl.

75. The compound of claim 1 which is (1RS,2RS,5SR)-2-{[(RS)- or -[(SR)-cyano-(3,4-dimethoxy-phenyl)-methyl]-carbamoyl}-3-aza-bicyclo[3.1.0]hexane-3-carboxylic acid benzyl ester.

76. The compound of claim 1 which is (S)-2-[(S)-(cyano-phenyl-methyl)-carbamoyl]-pyrrolidine-1-carboxylic acid benzyl ester.

77. The compound of claim 1 which is (S)-1-(3-methyl-butyryl)-pyrrolidine-2-carboxylic acid (R)- and (S)-(cyano-phenyl-methyl)-amide.

78. The compound of claim 1 which is (S)-2-1{(S)- and (R)-[cyano-(3-methoxy-phenyl)-methyl]-carbamoyl}-pyrrolidine-1-carboxylic acid benzyl ester.

79. The compound of claim 1 which is (S)-2-{(S)- and (R)-[cyano-(3-hydroxy-phenyl)-methyl]-carbamoyl}-pyrrolidine-1-carboxylic acid benzyl ester.

80. The compound of claim 1 which is (S)-2-[(R)- and (S)-(cyano-cyclopropyl-methyl)-carbamoyl]-pyrrolidine-1-carboxylic acid benzyl ester.

81. The compound of claim 1 which is (S)-1-benzylthiocarbamoyl-pyrrolidine-2-carboxylic acid ((R)- and (S)-benzo[1,3]dioxol-5-yl-cyano-methyl)-amide.

82. The compound of claim 1 which is (S)-1-benzylthiocarbamoyl-pyrrolidine-2-carboxylic acid [(R)- and (S)-cyano-(3,4-dimethoxy-phenyl)-methyl]-amide.

83. The compound of claim 1 which is (S)-1-benzylthiocarbamoyl-pyrrolidine-2-carboxylic acid [(R)- and (S)-(3-chloro-phenyl)-cyano-methyl]-amide.

84. The compound of claim 1 which is (S)-1-(3-fluoro-benzylthiocarbamoyl)-pyrrolidine-2-carboxylic acid [(R)- and (S)-(3-chloro-phenyl)-cyano-methyl]-amide.

85. The compound of claim 1 which is (S)-2-((R)- and (S)-1-cyano-3-phenyl-propylcarbamoyl)-pyrrolidine-1-carboxylic acid benzyl ester.

86. The compound of claim 1 which is (S)-2-[(R)- and (S)-(cyano-o-tolyl-methyl)-carbamoyl]-pyrrolidine-1-carboxylic acid benzyl ester.

87. The compound of claim 1 which is (S)-2-{(R)- and (S)-[cyano-(2,4-dimethoxy-phenyl)-methyl]-carbamoyl}-pyrrolidine-1-carboxylic acid benzyl ester.

88. The compound of claim 1 which is (S)-2-{(R)- and (S)-[cyano-(3-fluoro-phenyl)-methyl]-carbamoyl}-pyrrolidine-1-carboxylic acid benzyl ester.

89. The compound of claim 1 which is (S)-2-[(R)- and (S)-(cyano-m-tolyl-methyl)-carbamoyl]-pyrrolidine-1-carboxylic acid benzyl ester.

90. The compound of claim 1 which is (S)-2-{(R)- and (S)-[(4-bromo-phenyl)-cyano-methyl]-carbamoyl}-pyrrolidine-1-carboxylic acid benzyl ester.

91. The compound of claim 1 which is (S)-2-{(R)- and (S)-[cyano-(3,4,5-trimethoxy-phenyl)-methyl]carbamoyl}-pyrrolidine-1-carboxylic acid benzyl ester.

92. The compound of claim 1 which is (S)-2-{(R)- and (S)-[cyano-(3-phenoxy-phenyl)-methyl]-carbamoyl}-pyrrolidine-1-carboxylic acid benzyl ester.

93. The compound of claim 1 which is (S)-1-(naphthalene-2-sulfonyl)-pyrrolidine-2-carboxylic acid [(R)- and (S)-cyano-(3,4-dimethoxy-phenyl)-methyl]-amide.

94. The compound of claim 1 which is (S)-1-(naphthalene-1-sulfonyl)-pyrrolidine-2-carboxylic acid ((R)- and (S)-benzo[1,3]dioxol-5-yl-cyano-methyl)-amide.

95. The compound of claim 1 which is (S)-1-(5-dimethylamino-naphthalene-1-sulfonyl)-pyrrolidine-2-carboxylic acid [(R)- and (S)-cyano-(3,4-dimethoxy-phenyl)-methyl]-amide.

96. The compound of claim 1 which is (S)-1-(naphthalene-1-sulfonyl)-pyrrolidine-2-carboxylic acid [(R)- and (S)-cyano-(3,4-dimethoxy-phenyl)-methyl]-amide.

97. The compound of claim 1 which is (S)-1-(naphthalene-2-carbonyl)-pyrrolidine-2-carboxylic acid [(R)- and (S)-cyano-(3,4-dimethoxy-phenyl)-methyl]-amide.

98. The compound of claim 1 which is (S)-1-(naphthalene-1-carbonyl)-pyrrolidine-2-carboxylic acid [(R)- and (S)-cyano-(3,4-dimethoxy-phenyl)-methyl]-amide.

99. The compound of claim 1 which is (S)-1-(3-cyclopentyl-propionyl)-pyrrolidine-2-carboxylic acid [(R)- and (S)-cyano-(3,4-dimethoxy-phenyl)-methyl]-amide.

100. The compound of claim 1 which is (S)-1-benzyloxyacetyl-pyrrolidine-2-carboxylic acid [(R)- and (S)-cyano-(3,4-dimethoxy-phenyl)-methyl]-amide.

101. The compound of claim 1 which is (S)-1-(naphthalene-1-carbonyl)-pyrrolidine-2-carboxylic acid [(R)- and (S)-(3-chloro-phenyl)-cyano-methyl]-amide.

102. The compound of claim 1 which is (S)-1-(3-cyclopentyl-propionyl)-pyrrolidine-2-carboxylic acid [(R)- and (S)-(3-chloro-phenyl)-cyano-methyl]-amide.

103. The compound of claim 1 which is (S)-1-phenylacetyl-pyrrolidine-2-carboxylic acid [(R)- and (S)-(3-chloro-phenyl)-cyano-methyl]-amide.

104. The compound of claim 1 which is (S)-1-benzyloxyacetyl-pyrrolidine-2-carboxylic acid [(R)- and (S)-(3-chloro-phenyl)-cyano-methyl]-amide.

105. The compound of claim 1 which is (S)-pyrrolidine-1,2-dicarboxylic acid 2-{[(R)- and (S)-(3-chloro-phenyl)-cyano-methyl]-amide}1-[(R)-(1-naphthalen-1-yl-ethyl)-amide].

106. The compound of claim 1 which is (S)-1-(naphthalene-1-carbonyl)-pyrrolidine-2-carboxylic acid [(R)- and (S)-(3-bromo-phenyl)-cyano-methyl]-amide.

107. The compound of claim 1 which is (S)-1-phenylacetyl-pyrrolidine-2-carboxylic acid [(R)- and (S)-(3-bromo-phenyl)-cyano-methyl]-amide.

108. The compound of claim 1 which is (S)-1-benzyloxyacetyl-pyrrolidine-2-carboxylic acid [(R)- and (S)-(3-bromo-phenyl)-cyano-methyl]-amide.

109. The compound of claim 1 which is (S)-pyrrolidine-1,2-dicarboxylic acid 2-{[(R)- and (S)-(3-bromo-phenyl)-cyano-methyl]-amide}1-[(R)-(1-naphthalen-1-yl-ethyl)-amide].

110. The compound of claim 1 which is (S)-1-(3-cyclopentyl-propionyl)-pyrrolidine-2-carboxylic acid [(R)- and (S)-cyano-(3-methoxy-phenyl)-methyl]-amide.

111. The compound of claim 1 which is (S)-1-phenylacetyl-pyrrolidine-2-carboxylic acid [(R)- and (S)-cyano-(3-methoxy-phenyl)-methyl]-amide.

112. The compound of claim 1 which is (S)-1-benzyloxyacetyl-pyrrolidine-2-carboxylic acid [(R)- and (S)-cyano-(3-methoxy-phenyl)-methyl]-amide.

113. The compound of claim 1 which is 2-((R)- and (S)-1-cyano-3-phenyl-propylcarbamoyl)-pyrrolidine-1-carboxylic acid benzyl ester.

114. The compound of claim 1 which is (S)-2-{(R)- and (S)-[cyano-(3,4-dimethoxy-phenyl)-methyl]-carbamoyl}-pyrrolidine-1-carboxylic acid benzyl ester.

115. The compound of claim 1 which is (S)-1-(2-phenyl-ethenesulfonyl)-pyrrolidine-2-carboxylic acid ((R)- and (S)-benzo[1,3]dioxol-5-yl-cyano-methyl)-amide.

116. The compound of claim 1 which is (S)-pyrrolidine-1,2-dicarboxylic acid 2-{(R)- and (S)-[cyano-(3,4-dimethoxy-phenyl)-methyl]-amide}1-[(S)-(1-naphthalen-1-yl-ethyl)-amide].

117. The compound of claim 1 which is (S)-1-(2-phenyl-ethenesulfonyl)-pyrrolidine-2-carboxylic acid [(R)- and (S)-cyano-(3,4-dimethoxy-phenyl)-methyl]-amide.

118. The compound of claim 1 which is (S)-1-[2-(4-bromo-phenyl)-ethanoyl]-pyrrolidine-2-carboxylic acid [1-(3-chloro-phenyl)-1-cyano-methyl]-amide.

119. The compound of claim 1 which is (S)-1-[2-(4-iodo-phenyl)-ethanoyl]-pyrrolidine-2-carboxylic acid (1-benzo[1,3]dioxol-5-yl-1-cyano-methyl)-amide.

120. The compound of claim 1 which is (S)-1-[2-(4-fluoro-phenyl)-ethanoyl]-pyrrolidine-2-carboxylic acid [1-(3-chloro-phenyl)-1-cyano-methyl]-amide.

121. The compound of claim 1 which is (S)-1-(4-phenyl-butanoyl)-pyrrolidine-2-carboxylic acid [1-cyano-1-(3,4-dimethoxy-phenyl)-methyl]-amide.

122. The compound of claim 1 which is (S)-1-[2-(3-bromo-phenyl)-ethanoyl]-pyrrolidine-2-carboxylic acid [1-(3-chloro-phenyl)-1-cyano-methyl]-amide.

123. The compound of claim 1 which is (S)-1-(2-benzo[1,3]dioxol-5-yl-ethanoyl)-pyrrolidine-2-carboxylic acid [1-(3-chloro-phenyl)-1-cyano-methyl]-amide.

124. The compound of claim 1 which is (S)-1-(2-phenoxy-ethanoyl)-pyrrolidine-2-carboxylic acid [1-cyano-1-(3,4-dimethoxy-phenyl)-methyl]-amide.

125. The compound of claim 1 which is (S)-1-(2-o-tolyloxy-ethanoyl)-pyrrolidine-2-carboxylic acid [1-(3-chloro-phenyl)-1-cyano-methyl]-amide.

126. The compound of claim 1 which is (S)-1-(2-benzo[1,3]dioxol-5-yl-ethanoyl)-pyrrolidine-2-carboxylic acid (1-benzo[1,3]dioxol-5-yl-1-cyano-methyl)-amide.

127. The compound of claim 1 which is (S)-1-(2-phenoxy-ethanoyl)-pyrrolidine-2-carboxylic acid [1-(3-chloro-phenyl)-1-cyano-methyl]-amide.

128. The compound of claim 1 which is (S)-1-(2-phenyl-ethanoyl)-pyrrolidine-2-carboxylic acid [1-(3-chloro-phenyl)-1-cyano-methyl]-amide.

129. The compound of claim 1 which is (S)-1-[2-(4-fluoro-phenoxy)-ethanoyl]-pyrrolidine-2-carboxylic acid [1-cyano-1-(3,4-dimethoxy-phenyl)-methyl]-amide.

130. The compound of claim 1 which is (S)-1-(2-benzo[1,3]dioxol-5-yl-ethanoyl)-pyrrolidine-2-carboxylic acid [1-cyano-1-(3,4-dimethoxy-phenyl)-methyl]-amide.

131. The compound of claim 1 which is (S)-1-(3-phenyl-propanoyl)-pyrrolidine-2-carboxylic acid [1-cyano-1-(3,4-dimethoxy-phenyl)-methyl]-amide.

132. The compound of claim 1 which is (S)-1-[4-(3,4-dimethoxy-phenyl)-butanoyl]-pyrrolidine-2-carboxylic acid (1-benzo[1,3]dioxol-5-yl-1-cyano-methyl)-amide.

133. The compound of claim 1 which is (S)-1-[4-(3,4-dimethoxy-phenyl)-butanoyl]-pyrrolidine-2-carboxylic acid [1-(3-chloro-phenyl)-1-cyano-methyl]-amide.

134. The compound of claim 1 which is (S)-1-[2-(4-iodo-phenyl)-ethanoyl]-pyrrolidine-2-carboxylic acid [1-cyano-1-(3,4-dimethoxy-phenyl)-methyl]-amide.

135. The compound of claim 1 which is (S)-1-[4-(3,4-dimethoxy-phenyl)-butanoyl]-pyrrolidine-2-carboxylic acid [1-cyano-1-(3,4-dimethoxy-phenyl)-methyl]-amide.

136. The compound of claim 1 which is (S)-1-(3-1H-indol-3-yl-propanoyl)-pyrrolidine-2-carboxylic acid [1-cyano-1-(3,4-dimethoxy-phenyl)-methyl]-amide.

137. The compound of claim 1 which is (S)-1-(4-phenyl-butanoyl)-pyrrolidine-2-carboxylic acid (1-benzo[1,3]dioxol-5-yl-1-cyano-methyl)-amide.

138. The compound of claim 1 which is (S)-1-(2-phenylsulfanyl-ethanoyl)-pyrrolidine-2-carboxylic acid [1-(3-chloro-phenyl)-1-cyano-methyl]-amide.

139. The compound of claim 1 which is (S)-1-(4-cyclohexyl-butanoyl)-pyrrolidine-2-carboxylic acid [1-cyano-1-(3,4-dimethoxy-phenyl)-methyl]-amide.

140. The compound of claim 1 which is (S)-1-(3-cyclohexyl-propanoyl)-pyrrolidine-2-carboxylic acid (1-benzo[1,3]dioxol-5-yl-1-cyano-methyl)-amide.

141. The compound of claim 1 which is (S)-1-[4-(4-nitro-phenyl)-butanoyl]-pyrrolidine-2-carboxylic acid [1-cyano-1-(3,4-dimethoxy-phenyl)-methyl]-amide.

142. The compound of claim 1 which is (S)-1-[2-(4-iodo-phenyl)-ethanoyl]-pyrrolidine-2-carboxylic acid [1-(3-chloro-phenyl)-1-cyano-methyl]-amide.

143. The compound of claim 1 which is (S)-1-[2-(2,4-dimethyl-phenoxy)-ethanoyl]-pyrrolidine-2-carboxylic acid [1-(3-chloro-phenyl)-1-cyano-methyl]-amide.

144. The compound of claim 1 which is (S)-1-[4-(4-nitro-phenyl)-butanoyl]-pyrrolidine-2-carboxylic acid [1-(3-chloro-phenyl)--cyano-methyl]-amide.

145. The compound of claim 1 which is (S)-1-(1-naphthalen-1-yl-methanoyl)-pyrrolidine-2-carboxylic acid [1-(3-chloro-phenyl)-1-cyano-methyl]-amide.

146. The compound of claim 1 which is (S)-1-[2-(4-methoxy-phenoxy)-ethanoyl]-pyrrolidine-2-carboxylic acid [1-(3-chloro-phenyl)-1-cyano-methyl]-amide.

147. The compound of claim 1 which is (S)-1-(2-phenyl-ethanoyl)-pyrrolidine-2-carboxylic acid [1-cyano-1-(3,4-dimethoxy-phenyl)-methyl]-amide.

148. The compound of claim 1 which is (S)-1-[2-(2-methoxy-phenoxy)-ethanoyl]-pyrrolidine-2-carboxylic acid [1-cyano-1-(3,4-dimethoxy-phenyl)-methyl]-amide.

149. The compound of claim 1 which is (S)-1-[2-(4-methoxy-phenoxy)-ethanoyl]-pyrrolidine-2-carboxylic acid [1-cyano-1-(3,4-dimethoxy-phenyl)-methyl]-amide.

150. The compound of claim 1 which is (S)-1-(4-cyclohexyl-butanoyl)-pyrrolidine-2-carboxylic acid (1-benzo[1,3]dioxol-5-yl-1-cyano-methyl)-amide.

151. The compound of claim 1 which is (S)-1-{1-[1-(4-chloro-phenyl)-cyclopentyl]-methanoyl}-pyrrolidine-2-carboxylic acid [1-cyano-1-(3,4-dimethoxy-phenyl)-methyl]-amide.

152. The compound of claim 1 which is (S)-1-((Z)-3-phenyl-allanoyl)-pyrrolidine-2-carboxylic acid [1-cyano-1-(3,4-dimethoxy-phenyl)-methyl]-amide.

153. The compound of claim 1 which is (S)-1-(2-phenylsulfanyl-ethanoyl)-pyrrolidine-2-carboxylic acid [1-cyano-1-(3,4-dimethoxy-phenyl)-methyl]-amide.

154. The compound of claim 1 which is (S)-1-[2-(4-fluoro-phenoxy)-ethanoyl]-pyrrolidine-2-carboxylic acid [1-(3-chloro-phenyl)-1-cyano-methyl]-amide.

155. The compound of claim 1 which is (S)-1-[2-(3-methoxy-phenoxy)-ethanoyl]-pyrrolidine-2-carboxylic acid [1-cyano-1-(3,4-dimethoxy-phenyl)-methyl]-amide.

156. The compound of claim 1 which is (S)-1-(4-phenyl-butanoyl)-pyrrolidine-2-carboxylic acid [1-(3-chloro-phenyl)-1-cyano-methyl]-amide.

157. The compound of claim 1 which is (S)-1-[2-(3,4,5-trimethoxy-phenyl)-ethanoyl]-pyrrolidine-2-carboxylic acid [1-(3-chloro-phenyl)-1-cyano-methyl]-amide.

158. The compound of claim 1 which is (S)-1-(5-phenyl-pentanoyl)-pyrrolidine-2-carboxylic acid [1-cyano-1-(3,4-dimethoxy-phenyl)-methyl]-amide.

159. The compound of claim 1 which is (S)-1-(l-cyclopropyl-methanoyl)-pyrrolidine-2-carboxylic acid [1-cyano-1-(3,4-dimethoxy-phenyl)-methyl]-amide.

160. The compound of claim 1 which is (S)-1-[2-(4-fluoro-phenoxy)-ethanoyl]-pyrrolidine-2-carboxylic acid (1-benzo[1,3]dioxol-5-yl-1-cyano-methyl)-amide.

161. The compound of claim 1 which is (S)-1-[2-(4-chloro-phenoxy)-ethanoyl]-pyrrolidine-2-carboxylic acid [1-(3-chloro-phenyl)-1-cyano-methyl]-amide.

162. The compound of claim 1 which is (S)-1-(2-phenyl-ethanoyl)-pyrrolidine-2-carboxylic acid [1-(3-chloro-phenyl)-1-cyano-methyl]-amide.

163. The compound of claim 1 which is (S)-1-(3,3-diphenyl-propanoyl)-pyrrolidine-2-carboxylic acid [1-cyano-1-(3,4-dimethoxy-phenyl)-methyl]-amide.

164. The compound of claim 1 which is (S)-1-[2-(3-methoxy-phenoxy)-ethanoyl]-pyrrolidine-2-carboxylic acid (1-benzo[1,3]dioxol-5-yl-1-cyano-methyl)-amide.

165. The compound of claim 1 which is (S)-1-[2-(4-ethoxy-phenyl)-ethanoyl]-pyrrolidine-2-carboxylic acid (1-benzo[1,3]dioxol-5-yl-1-cyano-methyl)-amide.

166. The compound of claim 1 which is (S)-1-(5-phenyl-pentanoyl)-pyrrolidine-2-carboxylic acid [1-(3-chloro-phenyl)-1-cyano-methyl]-amide.

167. The compound of claim 1 which is (S)-1-(5-phenyl-pentanoyl)-pyrrolidine-2-carboxylic acid (1-benzo[1,3]dioxol-5-yl-1-cyano-methyl)-amide.

168. The compound of claim 1 which is (S)-1-[2-(2,4-dimethyl-phenoxy)-ethanoyl]-pyrrolidine-2-carboxylic acid (1-benzo[1,3]dioxol-5-yl-1-cyano-methyl)-amide.

169. The compound of claim 1 which is (S)-1-[2-(2-methoxy-phenoxy)-ethanoyl]-pyrrolidine-2-carboxylic acid (1-benzo[1,3]dioxol-5-yl-1-cyano-methyl)-amide.

170. The compound of claim 1 which is (S)-1-(3-cyclohexyl-propanoyl)-pyrrolidine-2-carboxylic acid [1-(3-chloro-phenyl)-1-cyano-methyl]-amide.

171. The compound of claim 1 which is (S)-1-[2-(3-methoxy-phenoxy)-ethanoyl]-pyrrolidine-2-carboxylic acid [1-(3-chloro-phenyl)-1-cyano-methyl]-amide.

172. The compound of claim 1 which is (S)-1-[3-(2,3,4-trimethoxy-phenyl)-propanoyl]-pyrrolidine-2-carboxylic acid [1-(3-chloro-phenyl)-1-cyano-methyl]-amide.

173. The compound of claim 1 which is (S)-1-(2-benzyloxy-ethanoyl)-pyrrolidine-2-carboxylic acid [1-(3-chloro-phenyl)-1-cyano-methyl]-amide.

174. The compound of claim 1 which is (S)-1-(1-cyclopropyl-methanoyl)-pyrrolidine-2-carboxylic acid [1-(3-chloro-phenyl)-1-cyano-methyl]-amide.

175. The compound of claim 1 which is (S)-1-[2-(2-methoxy-phenoxy)-ethanoyl]-pyrrolidine-2-carboxylic acid [1-(3-chloro-phenyl)-1-cyano-methyl]-amide.

176. The compound of claim 1 which is (S)-1-(1-cyclohexyl-methanoyl)-pyrrolidine-2-carboxylic acid [1-cyano-1-(3,4-dimethoxy-phenyl)-methyl]-amide.

177. The compound of claim 1 which is (S)-1-[2-(4-ethoxy-phenyl)-ethanoyl]-pyrrolidine-2-carboxylic acid [1-cyano-1-(3,4-dimethoxy-phenyl)-methyl]-amide.

178. The compound of claim 1 which is (S)-1-[3-(3,4,5-trimethoxy-phenyl)-propanoyl]-pyrrolidine-2-carboxylic acid [1-(3-chloro-phenyl)-1-cyano-methyl]-amide.

179. The compound of claim 1 which is (S)-1-(naphthalene-2-sulfonyl)-pyrrolidine-2-carboxylic acid [1-cyano-1-(3-phenoxy-phenyl)-methyl]-amide.

180. The compound of claim 1 which is (S)-1-(naphthalene-2-sulfonyl)-pyrrolidine-2-carboxylic acid (1-benzo[1,3]dioxol-5-yl-1-cyano-methyl)-amide.

181. The compound of claim 1 which is (S)-1-(3-cyclopentyl-propanoyl)-pyrrolidine-2-carboxylic acid [1-(3-chloro-phenyl)-1-cyano-methyl]-amide.

182. The compound of claim 1 which is (S)-1-(3-cyclopentyl-propanoyl)-pyrrolidine-2-carboxylic acid (1-benzo[1,3]dioxol-5-yl-1-cyano-methyl)-amide.

183. The compound of claim 1 which is (S)-1-(3-fluoro-benzylthiocarbamoyl)-pyrrolidine-2-carboxylic acid [1-cyano-1-(3,4-dimethoxy-phenyl)-methyl]-amide.

184. The compound of claim 1 which is (S)-1-[2-(2,4-dimethyl-phenoxy)-ethanoyl]-pyrrolidine-2-carboxylic acid [1-cyano-1-(3,4-dimethoxy-phenyl)-methyl]-amide.

* * * * *

UNITED STATES PATENT AND TRADEMARK OFFICE
CERTIFICATE OF CORRECTION

PATENT NO. : 6,531,612 B2
DATED : March 11, 2003
INVENTOR(S) : Tobias Gabriel, Michael Pech and Sabine Wallbaum It is certified that error appears in the above-identified patent and that said Letters Patent is hereby corrected as shown below:

Column 46,
Line 7, delete "(S)-2-1{(S)-" and insert -- (S)-2-{(S)- --

Column 49,
Line 9, delete "chloro-phenyl)--cyano-methyl]-amide." and insert
-- chloro-phenyl)-1-cyano-methyl]-amide. --

Signed and Sealed this

Nineteenth Day of August, 2003

JAMES E. ROGAN
*Director of the United States Patent and Trademark Office*